(12) United States Patent
Shimizu et al.

(10) Patent No.: US 8,748,452 B2
(45) Date of Patent: Jun. 10, 2014

(54) INDOLIZINE DERIVATIVE AND USE THEREOF FOR MEDICAL PURPOSES

(75) Inventors: Kazuo Shimizu, Azumino (JP); Masato Iizuka, Azumino (JP); Yasushi Takigawa, Azumino (JP)

(73) Assignee: Kissei Pharmaceutical Co., Ltd., Matsumoto-shi (JP)

( * ) Notice: Subject to any disclaimer, the term of this patent is extended or adjusted under 35 U.S.C. 154(b) by 195 days.

(21) Appl. No.: 13/259,621

(22) PCT Filed: Mar. 30, 2010

(86) PCT No.: PCT/JP2010/055692
§ 371 (c)(1),
(2), (4) Date: Sep. 23, 2011

(87) PCT Pub. No.: WO2010/113942
PCT Pub. Date: Oct. 7, 2010

(65) Prior Publication Data
US 2012/0015972 A1    Jan. 19, 2012

(30) Foreign Application Priority Data

Mar. 31, 2009 (JP) ................................. 2009-086306
Dec. 10, 2009 (JP) ................................. 2009-279976

(51) Int. Cl.
*A61K 31/437* (2006.01)
*A61P 13/12* (2006.01)
*A61P 19/02* (2006.01)
*C07D 471/04* (2006.01)

(52) U.S. Cl.
USPC .............. 514/294; 514/299; 546/112; 546/94

(58) Field of Classification Search
USPC ............................ 514/294, 299; 546/94, 112
See application file for complete search history.

(56) References Cited

U.S. PATENT DOCUMENTS

| | | | |
|---|---|---|---|
| 4,400,387 A | 8/1983 | Rosseels et al. | |
| 7,947,707 B2 | 5/2011 | Toyoshima et al. | |
| 8,003,647 B2 | 8/2011 | Shimizu et al. | |
| 2002/0006380 A1* | 1/2002 | Mignani et al. | 424/9.1 |
| 2009/0018104 A1 | 1/2009 | Sato et al. | |
| 2009/0306396 A1 | 12/2009 | Toyoshima et al. | |
| 2010/0056521 A1 | 3/2010 | Shimizu et al. | |
| 2010/0227864 A1 | 9/2010 | Shimizu et al. | |
| 2011/0230454 A1 | 9/2011 | Shimizu et al. | |

FOREIGN PATENT DOCUMENTS

| | | |
|---|---|---|
| WO | 2007/043400 A1 | 4/2007 |
| WO | 2007/043401 A1 | 4/2007 |
| WO | 2008/126898 A1 | 10/2008 |
| WO | 2008/126901 A1 | 10/2008 |
| WO | 2008/126899 A1 | 10/2011 |

OTHER PUBLICATIONS

Albertoni et al., Diseases of Renal Parenchyma, pp. 57-74.*
International Search Report of PCT/JP2010/055692, mailing date May 25, 2010 Previously presented.

* cited by examiner

*Primary Examiner* — Niloofar Rahmani
(74) *Attorney, Agent, or Firm* — Westerman, Hattori, Daniels & Adrian, LLP

(57) ABSTRACT

The present invention provides compounds useful as agents for the prevention or treatment of a disease associated with abnormal serum uric acid level and the like. That is, the present invention relates to indolizine derivatives represented by the following formula (I) having xanthine oxidase inhibitory activities and useful as agents for the prevention or treatment of a disease associated with abnormality of serum uric acid level, prodrugs thereof, salts thereof or the like. In the formula, ring U represents aryl or heteroaryl; $R^1$ represents halogen, a hydroxy group or the like; $R^2$ represents halogen, a hydroxy group, alkyl, alkoxy, alkyl substituted by fluorine, alkoxy substituted by fluorine or the like; m represents a number from 0 to 2; n represents a number from 0 to 3; and $R^3$ represents hydrogen, fluorine or the like.

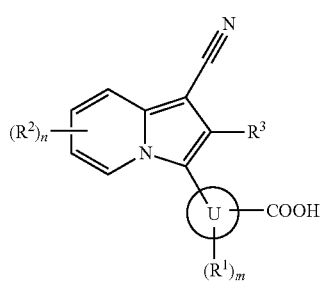

(I)

26 Claims, No Drawings

INDOLIZINE DERIVATIVE AND USE THEREOF FOR MEDICAL PURPOSES

TECHNICAL FIELD

The present invention relates to indolizine derivatives useful as medicaments.

More particularly, the present invention relates to indolizine derivatives having xanthine oxidase inhibitory activities and useful as agents for the prevention or treatment of a disease associated with abnormality of serum uric acid level, or prodrugs thereof, or pharmaceutically acceptable salts thereof.

BACKGROUND ART

Uric acid is the final product of purine metabolism in human. In many mammals, unlike human, uric acid is further broken down by urate oxidase (uricase) in the liver into allantoin, which is excreted through the kidney. In human, main pathway of uric acid excretion is the kidney, wherein approximately two thirds of uric acid is excreted in urine. The remaining is excreted in feces. When an excessive production or decreased excretion of uric acid occurs, that causes hyperuricemia. Hyperuricemia is classified into a uric acid overproduction type, a uric acid underexcretion type and a mixed type thereof. This classification of hyperuricemia is clinically important. Aiming for reducing adverse effects of therapeutic agents, therapeutic agents are chosen according to each class (for example, see Non-patent reference 1).

In hyperuricemia with a uric acid overproduction type, urinary excretion of uric acid increases, and when the urinary excretion of uric acid further increases by using of a uricosuric drug, the complication of urinary calculi is possibly developed. Therefore, in principle, allopurinol, a uric acid production inhibitor (or sometimes called a uric acid synthesis inhibitor, hereinafter referred to as "a uric acid production inhibitor"), is used in a uric acid overproduction type.

Uric acid is produced from purine bodies, which are derived from diet and synthesized endogenously, finally by oxidizing xanthine by xanthine oxidase. Allopurinol is developed as a xanthine oxidase inhibitor and an only uric acid production inhibitor used in medical practice. While allopurinol, however, is reported being effective in hyperuricemia and various diseases caused by the same, severe adverse effects such as poisoning syndrome (hypersensitivity angiitis), Stevens-Johnson syndrome, exfoliative dermatitis, aplastic anemia, liver dysfunction and the like have been also reported (for example, see Non-patent reference 2). As one of the causes, it has been pointed out that allopurinol has a nucleic acid-like structure and inhibits a pathway of pyrimidine metabolism (for example, see Non-patent reference 3).

On the other hand, in hyperuricemia with a uric acid underexcretion type, uric acid excretion decreases. It has been reported that when allopurinol, which is metabolized into oxypurinol to be excreted through the kidney by the same mechanism to uric acid, is used, the excretion of oxypurinol also decreases and that increases the incidence of liver disorders (for example, see Non-patent reference 4). Therefore, in principle, uricosuric drugs such as probenecid, benzbromarone and the like are used in a uric acid underexcretion type. These uricosuric drugs, however, also exert adverse effects such as gastrointestinal disorders, urinary calculi or the like. Particularly, benzbromarone is known as possibly causing fulminant hepatitis in the case of idiosyncratic patients (for example, see Non-patent references 5 and 6).

Thus, it is said that both of the existing uric acid production inhibitor and uricosuric drug have usage restrictions in patients or severe adverse effects. Therefore, the development of an easy-to-use agent for the treatment of hyperuricemia or the like has been desired.

Uric acid is eliminated mainly by the kidney, and the urate dynamics in the kidney has been investigated so far in some experiments using brush-border membrane vesicles (BBMV) prepared from the renal cortex (for example, see Non-patent references 7 and 8). It has been known that in human, uric acid is passed through the kidney glomerulus freely, and there are mechanisms of reabsorption and secretion of uric acid in the proximal tubule (for example, see Non-patent reference 9).

In recent years, the gene (SLC22A12) encoding the human kidney urate transporter has been identified (for example, see Non-patent reference 10). The transporter encoded by this gene (urate transporter 1, hereinafter referred to as "URAT1") is a 12-transmembrane type molecule belonging to OAT family. URAT1 mRNA was specifically expressed in the kidney, and localization of URAT1 in apical side of the proximal tubule was observed on the human kidney tissue section. In an experiment using xenopus oocyte expression system, uptake of uric acid through URAT1 was shown. Furthermore, it was shown that the uptake of uric acid is transported by exchange with organic anions such as lactic acid, pyrazinecarboxylic acid (PZA), nicotinic acid and the like, and the uric acid uptake through URAT1 is inhibited by uricosuric drugs, probenecid and benzbromarone. Thus, as expected by the experiment using membrane vesicles, it was strongly suggested that URAT1 is a urate/anion exchanger. That is, it was shown that URAT1 is a transporter that plays an important role in uric acid reabsorption in the kidney (for example, see Non-patent reference 10).

In addition, the relation between URAT1 and diseases became clear. Idiopathic renal hypouricemia is a disease wherein uric acid excretion is increased due to abnormal urate dynamics in the kidney and the serum uric acid level becomes low. It is known that the disease is often associated with urinary calculi or acute renal failure after exercise. URAT1 was identified as a causative gene of the renal hypouricemia (for example, see Non-patent reference 10). These things also strongly suggest that URAT1 is responsible for controlling the serum uric acid level.

Therefore, a substance having a URAT1 inhibitory activity is useful as an agent for the treatment and prevention of diseases associated with high serum uric acid levels, that is, hyperuricemia, gouty tophus, gouty arthritis, renal disorder associated with hyperuricemia, urinary calculi or the like.

In the treatment of hyperuricemia, it was reported that a combination of allopurinol of a uric acid production inhibitor and an agent having a uricosuric activity lowered the serum uric acid level more strongly than the single use of allopurinol (for example, see Non-patent references 11 and 12). Therefore, when treatment with an existing single agent can not exert effect enough, a higher therapeutic effect can be expected by a combination use of a uric acid production inhibitor and a uricosuric agent. Furthermore, for hyperuricemia with the uric acid underexcretion type, it is considered that since urinary excretion of uric acid can be decreased by lowering serum uric acid level, the risk of urinary calculi caused by the monotherapy with a uricosuric agent can be reduced. In addition, for hyperuricemia with the mixed type, high therapeutic effect is expected. Thus, an agent having both an inhibitory activity of uric acid production and a uricosuric activity is expected to become an extremely useful agent for the prevention or treatment of hyperuricemia or the like.

As a compound having both xanthine oxidase inhibitory activity and URAT1 inhibitory activity, morin, a natural product, is known (see Non-patent reference 13).

Benzoic acid or salicylic acid derivatives having xanthine oxidase inhibitory activity are known (see Patent references 1-5). However, in the references, anything is neither described nor suggested about indolizine derivatives of the present invention.

Patent reference 1: International Publication No. WO2007/043400 pamphlet
Patent reference 2: International Publication No. WO2007/043401 pamphlet
Patent reference 3: International Publication No. WO2008/126898 pamphlet
Patent reference 4: International Publication No. WO2008/126899 pamphlet
Patent reference 5: International Publication No. WO2008/126901 pamphlet
Non-patent reference 1: Atsuo Taniguchi and 1 person, *Modern Physician*, 2004, Vol.24, No.8, pp.1309-1312
Non-patent reference 2: Kazuhide Ogino and 2 persons, *Nippon Rinsho* (Japan Clinical), 2003, Vol.61, Extra edition 1, pp.197-201
Non-patent reference 3: Hideki Horiuchi and 6 persons, Life Science, 2000, Vol.66, No.21, pp.2051-2070
Non-patent reference 4: Hisashi Yamanaka and 2 persons, *Konyosankessyo to Tsufu* (Hyperuricemia and gout), issued by Medical Review Co., 1994, Vol.2, No.1, pp.103-111
Non-patent reference 5: Robert A Terkeltaub, N. Engl. J. Med., 2003, Vol.349, pp.1647-1655
Non-patent reference 6: Ming-Han H. Lee and 3 persons, Drug. Safety, 2008, Vol.31, pp.643-665
Non-patent reference 7: Francoise Roch-Ramel and 2 persons, Am. J. Physiol., 1994, Vol.266 (Renal Fluid Electrolyte Physiol., Vol.35), F797-F805
Non-patent reference 8: Francoise Roch-Ramel and 2 persons, J. Pharmacol. Exp. Ther., 1997, Vol.280, pp.839-845
Non-patent reference 9: Gim Gee Teng and 2 persons, Drugs, 2006, Vol.66, pp.1547-1563
Non-patent reference 10: Atsushi Enomoto and 18 persons, Nature, 2002, Vol.417, pp.447-452
Non-patent reference 11: S Takahashi and 5 persons, Ann. Rheum. Dis., 2003, Vol.62, pp.572-575
Non-patent reference 12: M. D. Feher and 4 persons, Rheumatology, 2003, Vol.42, pp.321-325
Non-patent reference 13: Zhifeng Yu and 2 persons, J. Pharmacol. Exp. Ther., 2006, Vol.316, pp.169-175

DISCLOSURE OF THE INVENTION

Problem That the Invention Aims to Solve

The problem of the present invention is to provide an agent which has an inhibitory activity of uric acid production for the prevention or treatment of a disease associated with abnormal serum uric acid level.

Means to Solve the Problem

The present inventors have studied earnestly to solve the above problem. As a result, it was found that indolizine derivatives represented by the following formula (I) exert an excellent xanthine oxidase inhibitory activity and extremely lower serum uric acid levels, and therefore, they can be a novel agent for the prevention or treatment of a disease associated with abnormal serum uric acid level, thereby forming the basis of the present invention.

That is, the present invention relates to:

[1] an indolizine derivative represented by the formula (I):

[Chem. 1]

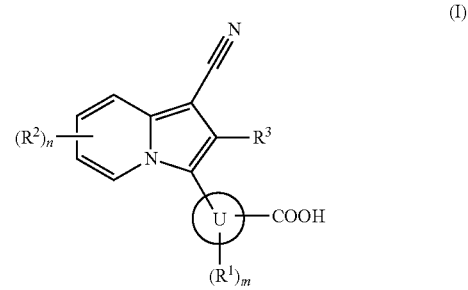

wherein
ring U represents aryl or heteroaryl;
$R^1$ represents a halogen atom, a hydroxy group, nitro, amino or $C_{1-6}$ alkyl which may be substituted by a fluorine atom;
$R^2$ represents any of the following (1) to (7):
(1) a halogen atom;
(2) a hydroxy group;
(3) amino;
(4) carbamoyl;
(5) cyano;
(6) carboxy;
(7) $C_{1-6}$ alkyl, $C_{2-6}$ alkenyl, $C_{2-6}$ alkynyl, $C_{1-6}$ alkoxy, mono(di)$C_{1-6}$ alkylamino, $C_{2-7}$ acyl, $C_{2-7}$ acylamino, mono(di)$C_{1-6}$ alkylcarbamoyl, $C_{1-6}$ alkylsulfonyl, $C_{1-6}$ alkylsulfonylamino, mono(di)$C_{1-6}$ alkylsulfamoyl, $C_{1-6}$ alkylthio, $C_{2-6}$ alkenyl $C_{1-6}$ alkoxy, $C_{3-8}$ cycloalkyl, 3 to 8-membered heterocycloalkyl, $C_{5-8}$ cycloalkenyl, 5 to 8-membered heterocycloalkenyl, $C_{3-8}$ cycloalkyloxy, $C_{3-8}$ cycloalkylamino, $C_{3-8}$ cycloalkyl $C_{1-6}$ alkyl, $C_{3-8}$ cycloalkyl $C_{1-6}$ alkoxy, $C_{3-8}$ cycloalkyl $C_{1-6}$ alkylamino, aryl, heteroaryl, aryloxy, arylamino, arylcarbonyl, arylcarbonylamino, aryl $C_{1-6}$ alkoxy, heteroaryloxy, heteroarylamino, heteroarylcarbonyl or heteroarylcarbonylamino each of which may have any group selected from substituent group α;
m represents an integral number from 0 to 2, and when m is 2, these $R^1$ are optionally different from each other;
n represents an integral number from 0 to 3, and when n is 2 or 3, these $R^2$ are optionally different from each other; and when two $R^2$ bound to the neighboring atoms in the indolizine ring exist and independently represent a group selected from the group consisting of $C_{1-6}$ alkyl which may be substituted by a fluorine atom and $C_{1-6}$ alkoxy which may be substituted by a fluorine atom, these two $R^2$ optionally form a 5 to 8-membered ring together with the binding atoms in the indolizine ring;
$R^3$ represents a hydrogen atom, a chlorine atom or a fluorine atom; and
substituent group α consists of a fluorine atom, a chlorine atom, a hydroxy group, amino, carboxy, carbamoyl, cyano, $C_{1-6}$ alkyl, $C_{1-6}$ alkoxy and mono(di)$C_{1-6}$ alkylamino, or a prodrug thereof, or a pharmaceutically acceptable salt thereof;
[2] an indolizine derivative as described in the above [1], represented by the formula (Ia):

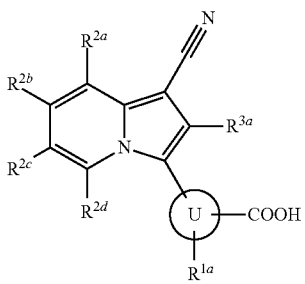

(Ia)

wherein
ring U represents aryl or heteroaryl;
$R^{1a}$ represents a hydrogen atom, a fluorine atom, a hydroxy group, amino, methyl or trifluoromethyl;
$R^{2a}$ and $R^{2b}$ independently represent any of the following (a1) to (a4):
  (a1) a hydrogen atom;
  (a2) a halogen atom;
  (a3) a hydroxy group;
  (a4) $C_{1-6}$ alkyl, $C_{1-6}$ alkoxy, mono(di)$C_{1-6}$ alkylamino, $C_{2-7}$ acyl, $C_{1-6}$ alkylthio, $C_{3-8}$ cycloalkyl, 3 to 8-membered heterocycloalkyl, aryl or heteroaryl each of which may have any group selected from substituent group α;

$R^{2c}$ represents a hydrogen atom, a halogen atom, a hydroxy group, $C_{1-6}$ alkyl which may have any group selected from substituent group α or $C_{1-6}$ alkoxy which may have any group selected from substituent group α; or when $R^{2a}$ and $R^{2b}$, or $R^{2b}$ and $R^{2c}$ independently represent a group selected from the group consisting of $C_{1-6}$ alkyl which may be substituted by a fluorine atom and $C_{1-6}$ alkoxy which may be substituted by a fluorine atom, they optionally form a 5 to 8-membered ring together with the binding atoms in the indolizine ring;

$R^{2d}$ represents a hydrogen atom or a fluorine atom;
$R^{3a}$ represents a hydrogen atom or a fluorine atom; and
substituent group α has the same meaning as described in the above [1], or a prodrug thereof, or a pharmaceutically acceptable salt thereof;

[3] an indolizine derivative as described in the above [2], wherein ring U represents a benzene ring, a pyridine ring, a thiophene ring or a thiazole ring, or a prodrug thereof, or a pharmaceutically acceptable salt thereof;

[4] an indolizine derivative as described in the above [2], wherein the group represented by the formula:

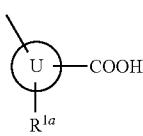

[Chem.3]

is a group represented by the formula:

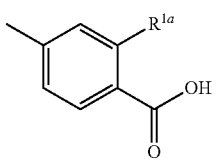

[Chem.4]

and $R^{1a}$ represents a hydrogen atom or a hydroxy group, or a prodrug thereof, or a pharmaceutically acceptable salt thereof;

[5] an indolizine derivative as described in the above [3] or [4], wherein $R^{2a}$ and $R^{2b}$ independently represent any of the following (b1) to (b4):
  (b1) a hydrogen atom;
  (b2) a halogen atom;
  (b3) a hydroxy group;
  (b4) $C_{1-6}$ alkyl, $C_{1-6}$ alkoxy, mono(di)$C_{1-6}$ alkylamino or hydroxy$C_{1-6}$ alkyl each of which may be substituted by a fluorine atom; and $R^{2c}$ represents a hydrogen atom, a halogen atom, a hydroxy group, $C_{1-6}$ alkyl which may be substituted by a fluorine atom or $C_{1-6}$ alkoxy which may be substituted by a fluorine atom, or a prodrug thereof, or a pharmaceutically acceptable salt thereof;

[6] an indolizine derivative as described in any one of the above [2] to [5], wherein $R^{2d}$ represents a hydrogen atom, or a prodrug thereof, or a pharmaceutically acceptable salt thereof;

[7] an indolizine derivative as described in any one of the above [1] to [6], wherein $R^3$ or $R^{3a}$ represents a hydrogen atom, or a prodrug thereof, or a pharmaceutically acceptable salt thereof;

[8] an indolizine derivative as described in the above [6] or [7], wherein $R^{1a}$ represents a hydrogen atom or a hydroxy group;
$R^{2a}$ represents a hydrogen atom, a fluorine atom, a chlorine atom, methyl, ethyl, methoxy, monofluoromethyl, difluoromethyl, trifluoromethyl, difluoromethoxy or trifluoromethoxy;
$R^{2b}$ represents a hydrogen atom, a fluorine atom, a chlorine atom, methyl, ethyl, methoxy, monofluoromethyl, difluoromethyl, trifluoromethyl, difluoromethoxy or trifluoromethoxy; and
$R^{2c}$ represents a hydrogen atom, a fluorine atom, a chlorine atom, methyl, monofluoromethyl, difluoromethyl or trifluoromethyl, or a prodrug thereof, or a pharmaceutically acceptable salt thereof;

[9] an indolizine derivative as described in the above [8], wherein $R^{2b}$ represents a hydrogen atom, methyl, ethyl, methoxy, monofluoromethyl, difluoromethyl, trifluoromethyl, difluoromethoxy or trifluoromethoxy, or a prodrug thereof, or a pharmaceutically acceptable salt thereof;

[10] an indolizine derivative as described in the above [8] or [9], wherein $R^{1a}$ represents a hydrogen atom, or a prodrug thereof, or a pharmaceutically acceptable salt thereof;

[11] an indolizine derivative as described in the above [8] or [9], wherein $R^{1a}$ represents a hydroxy group, or a prodrug thereof, or a pharmaceutically acceptable salt thereof;

[12] an indolizine derivative as described in any one of the above [1] to [11], which is a xanthine oxidase inhibitor, or a prodrug thereof, or a pharmaceutically acceptable salt thereof;

[13] a pharmaceutical composition comprising as an active ingredient an indolizine derivative as described in any one of the above [1] to [11], or a prodrug thereof, or a pharmaceutically acceptable salt thereof;

[14] a pharmaceutical composition as described in the above [13], which is an agent for the prevention or treatment of a disease selected from the group consisting of hyperuricemia, gouty tophus, gouty arthritis, renal disorder associated with hyperuricemia and urinary calculi;

[15] a pharmaceutical composition as described in the above [14], which is an agent for the prevention or treatment of hyperuricemia;

[16] a pharmaceutical composition as described in the above [13], which is an agent for lowering serum uric acid level;

[17] a pharmaceutical composition as described in the above [13], which is a uric acid production inhibitor; and the like.

In the indolizine derivative represented by the formula (I) of the present invention, each term has the following meaning unless otherwise specified.

The term "halogen atom" means a fluorine atom, a chlorine atom, a bromine atom or an iodine atom.

The term "$C_{1-6}$ alkyl" means a straight-chained or a branched alkyl group having 1 to 6 carbon atoms, and methyl, ethyl, propyl, isopropyl, butyl, isobutyl, sec-butyl, tert-butyl and the like can be illustrated.

The term "$C_{1-6}$ alkylene" means a divalent group derived from the above $C_{1-6}$ alkyl.

The term "$C_{2-6}$ alkenyl" means a straight-chained or a branched alkenyl group having 2 to 6 carbon atoms, and vinyl, allyl, 1-propenyl, isopropenyl and the like can be illustrated.

The term "$C_{2-6}$ alkynyl" means a straight-chained or a branched alkynyl group having 2 to 6 carbon atoms, and ethynyl, 2-propynyl and the like can be illustrated.

The term "$C_{1-6}$ alkoxy" means a straight-chained or a branched alkoxy group having 1 to 6 carbon atoms, and methoxy, ethoxy, propoxy, isopropoxy and the like can be illustrated.

The term "hydroxy$C_{1-6}$ alkyl" means a straight-chained or a branched hydroxyalkyl group having 1 to 6 carbon atoms.

The term "$C_{1-6}$ alkylsulfonyl" means a group represented by ($C_{1-6}$ alkyl)-$SO_2$—, and methylsulfonyl, ethylsulfonyl and the like can be illustrated.

The term "$C_{1-6}$ alkylsulfonylamino" means a group represented by ($C_{1-6}$ alkyl)-$SO_2NH$—, and methylsulfonylamino, ethylsulfonylamino and the like can be illustrated.

The term "$C_{2-7}$ acyl" means a straight-chained or a branched acyl group having 2 to 7 carbon atoms, and acetyl, propionyl, butyryl, isobutyryl, pivaloyl and the like can be illustrated.

The term "$C_{2-7}$ acylamino" means a group represented by ($C_{1-6}$ alkyl)-C(O)NH—.

The term "$C_{1-6}$ alkylthio" means a group represented by ($C_{1-6}$ alkyl)-S—.

The term "$C_{2-6}$ alkenyl $C_{1-6}$ alkoxy" means the above $C_{1-6}$ alkoxy substituted by the above $C_{2-6}$ alkenyl.

The term "mono(di)$C_{1-6}$ alkylamino" means amino mono- or di-substituted by the above $C_{1-6}$ alkyl.

The term "mono(di)$C_{1-6}$ alkylsulfamoyl" means sulfamoyl mono- or di-substituted by the above $C_{1-6}$ alkyl.

The term "mono(di)$C_{1-6}$ alkylcarbamoyl" means carbamoyl mono- or di-substituted by the above $C_{1-6}$ alkyl.

These substituents may be different from each other in the case of di-substitution.

The term "$C_{3-8}$ cycloalkyl" means a 3 to 8-membered saturated cyclic hydrocarbon group, and cyclopropyl, cyclobutyl, cyclopentyl, cyclohexyl, cycloheptyl or cyclooctyl can be illustrated.

The term "$C_{5-8}$ cycloalkenyl" means a 5 to 8-membered cycloalkenyl group, and cyclopentenyl, cyclohexenyl, cycloheptenyl, cyclooctenyl and the like can be illustrated.

The term "3 to 8-membered heterocycloalkyl" means a 3 to 8-membered heterocycloalkyl group having the same or different 1 or 2 hetero atoms selected from an oxygen atom, a sulfur atom and a nitrogen atom in the ring, and aziridino, azetidino, morpholino, 2-morpholinyl, thiomorpholino, 1-pyrrolidinyl, piperidino, 4-piperidinyl, 1-piperazinyl, 1-pyrrolyl, tetrahydrofuranyl, tetrahydropyranyl and the like can be illustrated.

The term "5 to 8-membered heterocycloalkenyl" means a 5 to 8-membered heterocycloalkenyl group having the same or different 1 or 2 hetero atoms selected from an oxygen atom, a sulfur atom and a nitrogen atom in the ring, and dihydrofuranyl, dihydrothiophenyl, dihydropyrrolyl, oxathionyl and the like can be illustrated.

The term "$C_{3-8}$ cycloalkyloxy" means a group represented by ($C_{3-8}$ cycloalkyl)-O—.

The term "$C_{3-8}$ cycloalkylamino" means a group represented by ($C_{3-8}$ cycloalkyl)-NH—.

The term "$C_{3-8}$ cycloalkyl $C_{1-6}$ alkyl" means the above $C_{1-6}$ alkyl substituted by the above $C_{3-8}$ cycloalkyl.

The term "$C_{3-8}$ cycloalkyl $C_{1-6}$ alkoxy" means the above $C_{1-6}$ alkoxy substituted by the above $C_{3-8}$ cycloalkyl.

The term "$C_{3-8}$ cycloalkyl $C_{1-6}$ alkylamino" means a group represented by ($C_{1-6}$ alkyl)-NH— substituted by the above $C_{3-8}$ cycloalkyl.

The term "aryl" means phenyl.

The term "aryloxy" means a group represented by (aryl)-O—.

The term "arylamino" means a group represented by (aryl)-NH—.

The term "arylcarbonyl" means a group represented by (aryl)-C(O)—.

The term "arylcarbonylamino" means a group represented by (aryl)-C(O)NH—.

The term "aryl $C_{1-6}$ alkoxy" means the above $C_{1-6}$ alkoxy substituted by the above aryl.

The term "heteroaryl" means a 5 or 6-membered aromatic heterocyclic group having the same or different 1 to 4 hetero atoms selected from an oxygen atom, a sulfur atom and a nitrogen atom in the ring, and thiazolyl, oxazolyl, isothiazolyl, isoxazolyl, pyridyl, pyrimidyl, pyrazyl, pyridazyl, pyrrolyl, furanyl, thiophenyl, imidazolyl, pyrazolyl, oxadiazolyl, thiadiazolyl, triazolyl, tetrazolyl, furazanyl and the like can be illustrated.

The term "heteroaryloxy" means a group represented by (heteroaryl)-O—.

The term "heteroarylamino" means a group represented by (heteroaryl)-NH—.

The term "heteroarylcarbonyl" means a group represented by (heteroaryl)-C(O)—.

The term "heteroarylcarbonylamino" means a group represented by (heteroaryl)-C(O)NH—.

As a 5 to 8-membered ring two $R^2$, $R^{2a}$ and $R^{2b}$, or $R^{2b}$ and $R^{2c}$ optionally form together with the binding atoms in the indolizine ring, for example, cyclopentyl, cyclohexyl, [1,4]dioxyl, [1,3]dioxolyl and the like each of which may have methyl or methoxy on the ring can be illustrated.

The term "may be substituted by a fluorine atom" means optionally having 1 to 5 fluorine atoms as substituent. In addition, when the group which may be substituted by a fluorine atom is methyl, methoxy or N-methylamino, it means optionally having 1 to 3 fluorine atoms, or in case of hydroxymethyl, it means optionally having 1 or 2 fluorine atoms.

The term "may have any group selected from substituent group α" means optionally having 1 to 3 same or different groups selected from substituent group α, and having none or 1 substituent is preferred. With the proviso that when the group selected from substituent group α is a fluorine atom, it has the same meaning of the above "may be substituted by a fluorine atom".

The term "mono(di)hydroxy $C_{1-6}$ alkyl" means the above $C_{1-6}$ alkyl substituted by 1 or 2 hydroxy groups.

The term "$C_{1-6}$ alkoxy $C_{1-6}$ alkoxy $C_{1-6}$ alkyl" means the above $C_{1-6}$ alkyl substituted by the above $C_{1-6}$ alkoxy substituted by the above $C_{1-6}$ alkoxy.

The term "mono(di)$C_{1-6}$ alkylamino $C_{1-6}$ alkyl" means the above $C_{1-6}$ alkyl substituted by the above mono(di) $C_{1-6}$ alkylamino.

The term "3 to 8-membered heterocycloalkyl $C_{1-6}$ alkyl" means the above $C_{1-6}$ alkyl substituted by the above 3 to 8-membered heterocycloalkyl.

The term "amino $C_{1-6}$ alkylene" means the above $C_{1-6}$ alkylene substituted by an amino group.

As one of the preferred embodiments in the present invention, for example, an indolizine derivative represented by the following general formula (IA) can be illustrated.

[Chem. 5]

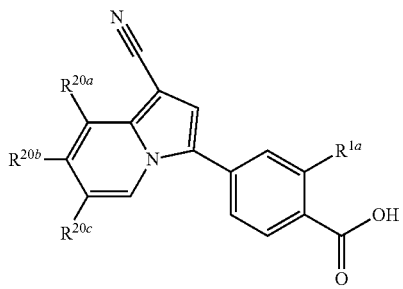

(IA)

In the formula, $R^{1a}$ represents a hydrogen atom or a hydroxy group; $R^{20a}$ represents a hydrogen atom, a fluorine atom, a chlorine atom, methyl or methoxy; $R^{20b}$ represents a hydrogen atom, a chlorine atom, methyl, ethyl, methoxy, monofluoromethyl or trifluoromethyl; and $R^{20c}$ represents a hydrogen atom, a fluorine atom, a chlorine atom, methyl or trifluoromethyl.

Also, as another preferred embodiment, an indolizine derivative represented by the following general formula (IB) can be illustrated.

[Chem. 6]

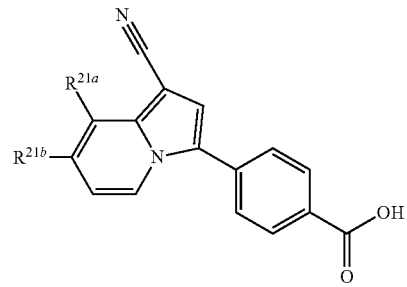

(IB)

In the formula, $R^{21a}$ represents a hydrogen atom, a fluorine atom or a chlorine atom; and $R^{21b}$ represents a hydrogen atom, methyl, monofluoromethyl or trifluoromethyl.

Also, as another preferred embodiment, an indolizine derivative represented by the following general formula (IC) can be illustrated.

[Chem. 7]

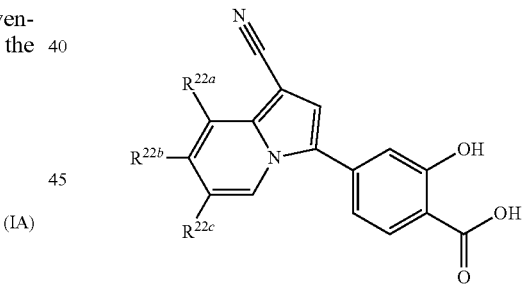

(IC)

In the formula, $R^{22a}$ represents a hydrogen atom or a fluorine atom; $R^{22b}$ represents a hydrogen atom, methyl, methoxy, monofluoromethyl or trifluoromethyl; and $R^{22c}$ represents a hydrogen atom, a fluorine atom, a chlorine atom, methyl or trifluoromethyl.

An indolizine derivative represented by the formula (I) of the present invention can be prepared, for example, by a method described below or a similar method thereto, or a method described in literatures or a similar method thereto and the like. In addition, when a protective group is necessary, operations of introduction and deprotection can be also conducted optionally in combination according to a general method. Each reaction can be also optionally conducted by using a pressure-resistant reaction container.

Synthetic Method 1

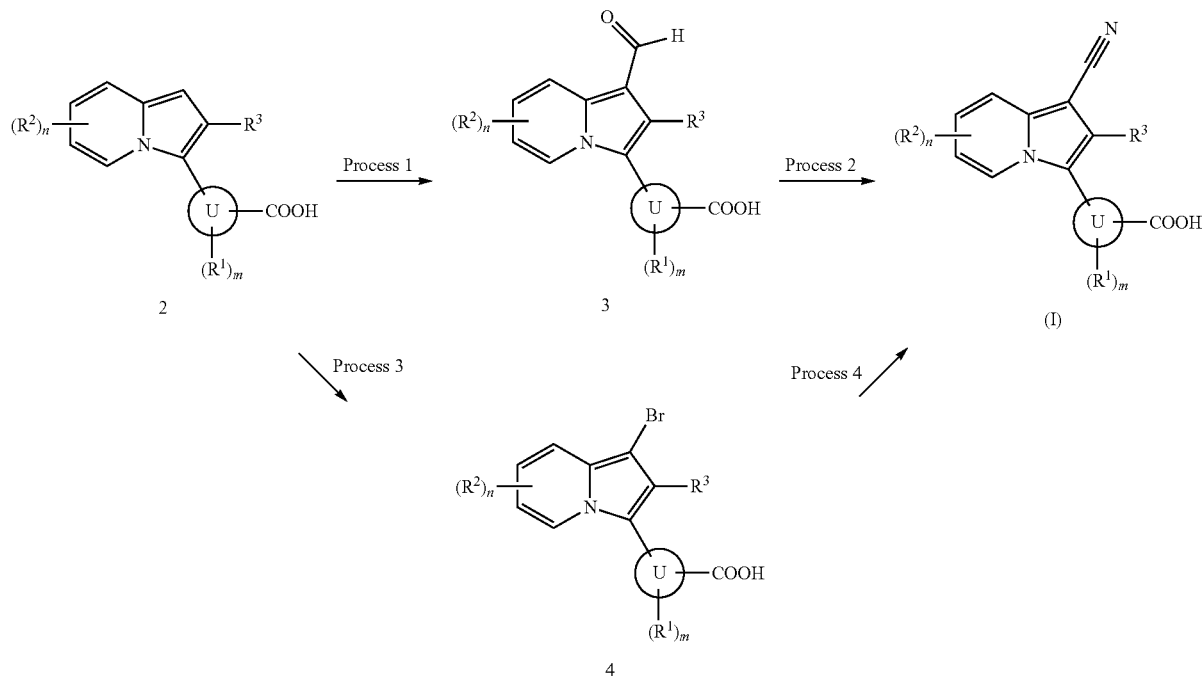

In the formula, ring U, $R^1$, $R^2$, $R^3$, m and n have the same meanings as defined above.

Process 1

Aldehyde compound (3) can be also prepared by subjecting Compound (2) to formylation in an inert solvent in the presence of N, N-dimethylformamide and phosphoryl chloride. As the inert solvent, N, N-dimethylformamide, benzene, toluene, chlorobenzene, dichloromethane, 1, 2-dichloroethane, chloroform, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 2

An indolizine derivative represented by the formula (I) of the present invention can be also prepared by subjecting Aldehyde compound (3) to cyanation using an hydroxylamine or a hydrochloride salt thereof in an inert solvent in the presence or absence of a base in the presence or absence of a condensation agent. As the inert solvent, N, N-dimethylformamide, acetonitrile, benzene, toluene, chlorobenzene, dichloromethane, 1, 2-dichloroethane, chloroform, tetrahydrofuran, 1, 4-dioxane, N-methylpyrrolidone, a mixed solvent thereof and the like can be illustrated. As the base, triethylamine, N, N-diisopropylethylamine, pyridine, 2, 6-lutidine, 1, 8-diazabicyclo[5, 4, 0]-7-undecene, potassium carbonate, sodium carbonate and the like can be illustrated. As the condensation agent, acetic anhydride, thionyl chloride, phosphorous pentachloride, N, N-dicyclohexylcarbodiimide, N, N'-carbonylimidazole and the like can be illustrated. The reaction temperature is usually at 0° C. to reflux temperature, and the reaction time is usually from 30 minutes to 7 days, varying based on a used starting material, solvent and reaction temperature or the like.

The above cyanation reaction can be conducted by allowing Aldehyde compound (3) and hydroxylamine or a hydrochloride salt thereof to react with sodium formate in formic acid solvent. The reaction temperature is usually at 0° C. to reflux temperature, and the reaction time is usually from 30 minutes to 7 days, varying based on a used starting material, solvent and reaction temperature or the like.

Process 3

Brominated compound (4) can be also prepared by subjecting Compound (2) to bromination in the presence of a bromination agent such as N-bromosuccinimide or the like in an inert solvent. As the inert solvent, dichloromethane, 1, 2-dichloroethane, chloroform, carbontetrachloride, acetic acid, acetonitrile, methanol, dimethylformamide, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 4

An indolizine derivative represented by the formula (I) of the present invention can be also prepared by subjecting Brominated compound (4) to cyanation in the presence of a palladium catalyst and zinc cyanide in an inert solvent. As the inert solvent, benzene, toluene, xylene, diethylether, tetrahydrofuran, 1, 4-dioxane, 1, 2-dimethoxyethane, dichloromethane, 1, 2-dichloroethane, chloroform, methanol, ethanol, 2-propanol, butanol, N, N-dimethylformamide, N-methylpyrrolidone, dimethylsulfoxide, water, a mixed solvent thereof and the like can be illustrated. As the palladium catalyst, tetrakis(triphenylphosphine)palladium, dichlorobis(triphenyl-phosphine)palladium, 1, 1'-bis(diphenylphosphino)ferrocene-palladium dichloride and the like can be illustrated. The reaction temperature is usually at 0° C. to reflux temperature, and the reaction time is usually from 30 minutes to 7 days, varying based on a used starting material, solvent and reaction temperature or the like.

Among the indolizine derivatives represented by the formula (I) of the present invention, an indolizine derivative (Ib) wherein $R^3$ represents a hydrogen atom can be also prepared by the methods of the following Synthetic methods 2 and 3.

Synthetic Method 2

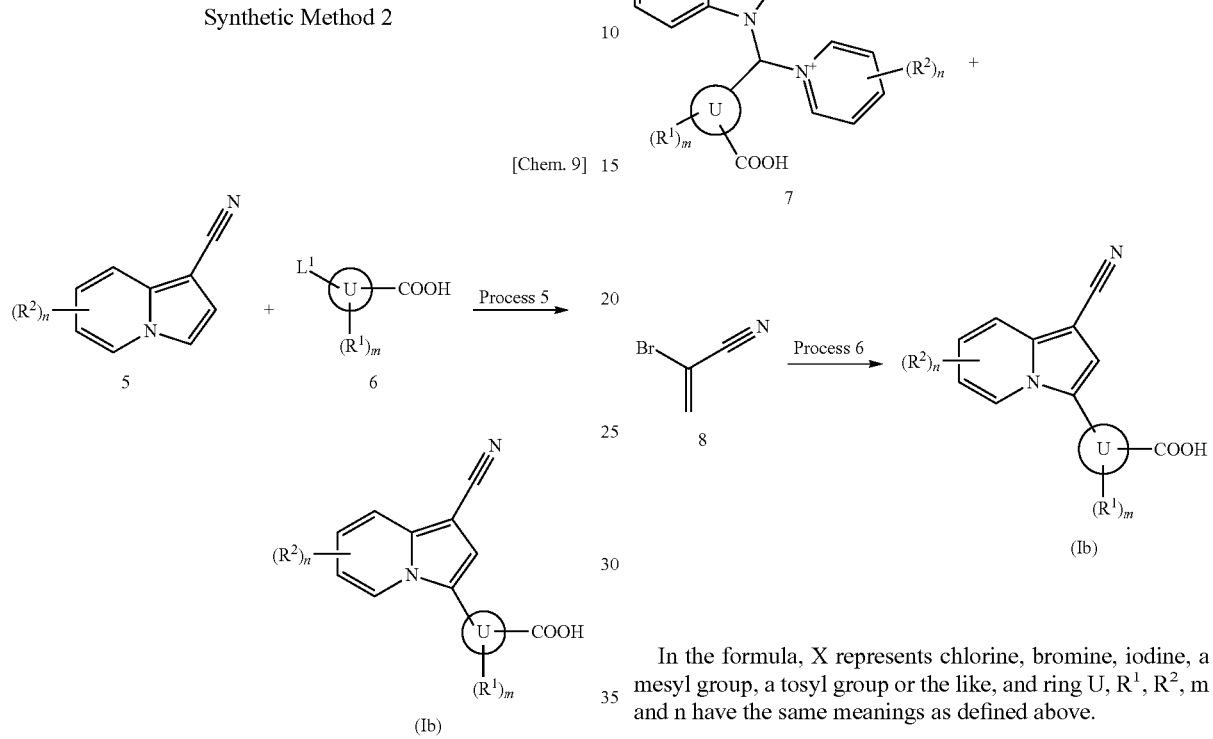

In the formula, $L^1$ represents a leaving group such as a chlorine atom, a bromine atom, an iodine atom, a trifluoromethanesulfonyloxy group or the like, and ring U, $R^1$, $R^2$, m and n have the same meanings as defined above.

Process 5

An indoliline derivative (Ib) of the present invention can be also prepared by conducting coupling reaction of indolizine compound (5) and Compound (6) in an inert solvent in the presence of a base and a palladium catalyst. As the inert solvent, benzene, toluene, xylene, diethylether, tetrahydrofuran, 1, 4-dioxane, 1, 2-dimethoxy-ethane, dichloromethane, 1, 2-dichloroethane, chloroform, N, N-dimethylformamide, N-methylpyrrolidone, dimethylsulfoxide, water, a mixed solvent thereof and the like can be illustrated. As the base, sodium acetate, potassium acetate, sodium carbonate, potassium carbonate, cesium carbonate, sodium hydroxide, potassium hydroxide, lithium hydroxide, sodium ethoxide, sodium methoxide, potassium fluoride, cesium fluoride, triethylamine, N, N-diisopropylethylamine, pyridine, 2, 6-lutidine, 1, 8-diaza-bicyclo[5, 4, 0]-7-undecene and the like can be illustrated. As the palladium catalyst, dichlorobis(triphenylphosphine)palladium, palladium acetate and the like can be illustrated. The reaction temperature is usually at 0° C. to reflux temperature, and the reaction time is usually from 30 minutes to 7 days, varying based on a used starting material, solvent and reaction temperature or the like.

Synthetic Method 3

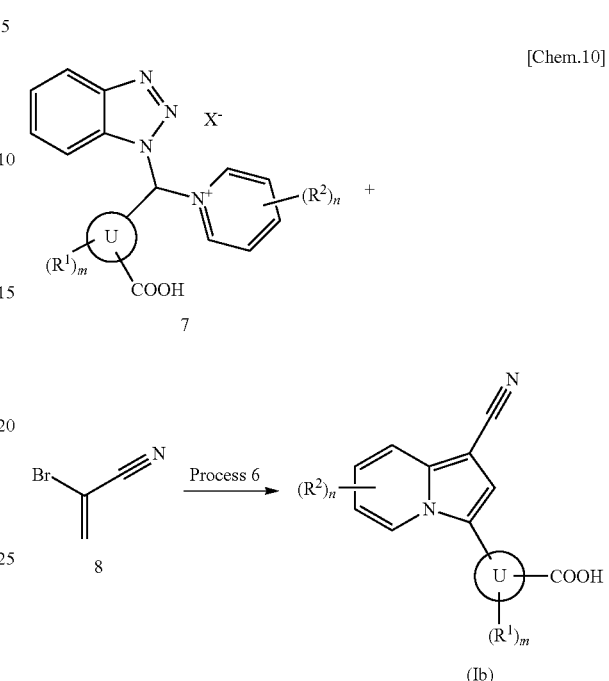

In the formula, X represents chlorine, bromine, iodine, a mesyl group, a tosyl group or the like, and ring U, $R^1$, $R^2$, m and n have the same meanings as defined above.

Process 6

An indolizine derivative (Ib) of the present invention can be also prepared by allowing Benzotriazole compound (7) to react with 2-bromoacrylonitrile (8) in an inert solvent in the presence of a base. As the inert solvent, acetonitrile, tetrahydrofuran, N, N-dimethylformamide, diethylether, N-methylpyrrolidone, ethanol, methanol, water, a mixed solvent thereof and the like can be illustrated. As the base, sodium hydroxide, potassium hydroxide, sodium hydride, potassium tert-butoxide, sodium methoxide, sodium ethoxide, lithium diisopropylamide, triethylamine, N, N-diisopropylethylamine and the like can be illustrated. The reaction temperature is usually at 0° C. to reflux temperature, and the reaction time is usually from 30 minutes to 7 days, varying based on a used starting material, solvent and reaction temperature or the like.

Compound (2) used in the above Synthetic method 1 can be also prepared by using various indolizine compounds by a method described in literature (for example, Choul-Hong Park, Org.Lett., 2004, 6, pp.1159-1162 or the like) or a similar method thereto or the like. The indolizine compounds used in this method can be also prepared by a method described in literature (for example, David, Virieux, Tetrahedron, 2006, 62, pp.3710-3720 or the like) or a similar method thereto and the like.

In Compound (2) used in the above Synthetic method 1, Compound (2a) wherein $R^3$ represents a fluorine atom can be also prepared by the method of the following Synthetic method 4.

Synthetic Method 4

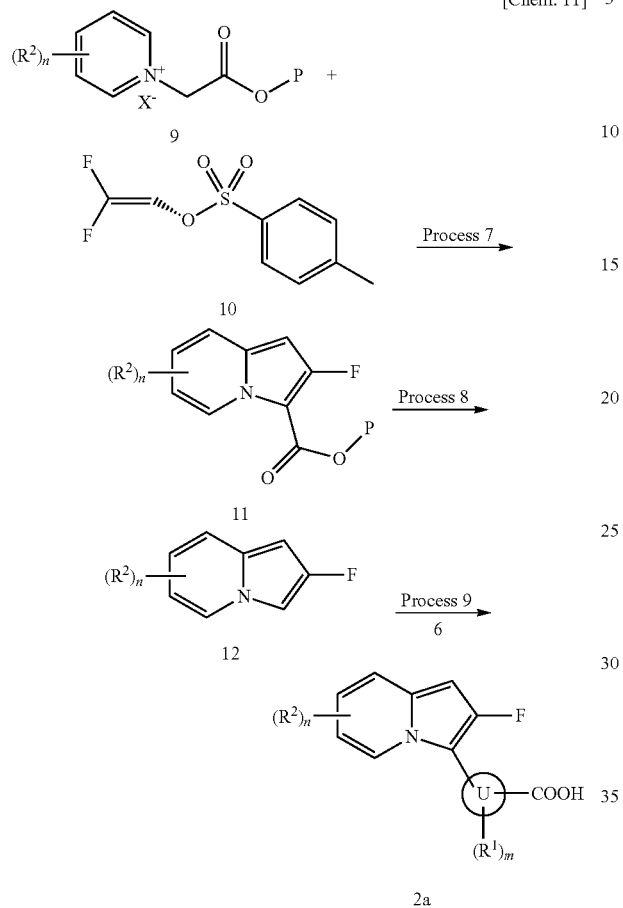

In the formula, P represents a protective group, and ring U, $R^1$, $R^2$, m, n and X have the same meanings as defined above.

Process 7

Compound (11) can be also prepared by allowing Compound (9) to react with Compound (10) in an inert solvent in the presence of a base. As the inert solvent, N, N-dimethylformamide, N-methylpyrrolidone, dimethylsulfoxide, diethyl ether, tetrahydrofuran, 1, 4-dioxane, 1, 2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, potassium fluoride, cesium fluoride, triethylamine, pyridine, N, N-diisopropylethylamine, 2, 6-lutidine, 1, 8-diazabicyclo[5, 4, 0]-7-undecene and the like can be illustrated. The reaction temperature is usually at 0° C. to reflux temperature, and the reaction time is usually from 30 minutes to 7 days, varying based on a used starting material, solvent and reaction temperature or the like.

Process 8

Compound (12) can be also prepared by removing the protective group of Compound (11) and subjecting the obtained carboxylic acid compound to decarboxylation in an inert solvent in the presence or absence of a catalyst. As the inert solvent, quinoline, metaphosphoric acid, acetic acid, trifluoroacetic acid, hydrochloric acid, sulfuric acid, methanol, a mixed solvent thereof and the like can be illustrated. As the catalyst, copper and the like can be illustrated. The reaction temperature is usually at 0° C. to reflux temperature, and the reaction time is usually from 30 minutes to 7 days, varying based on a used starting material, solvent and reaction temperature or the like.

Process 9

Compound (2a) can be also prepared by conducting coupling of Compound (12) and the above Compound (6) by a method similar to the above Process 5.

Indolizine compound (5) used in the above Synthetic method 2 can be also prepared, for example, by the methods of the following Synthetic methods 5 and 6.

Synthetic Method 5

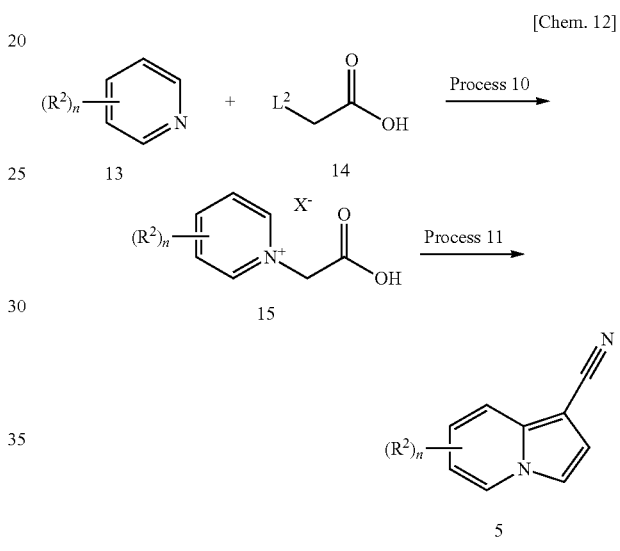

In the formula, $L^2$ represents a leaving group such as a chlorine atom, a bromine atom, an iodine atom, a mesyl group, a tosyl group and the like, and $R^2$, n and X have the same meanings as defined above.

Process 10

Compound (15) can be also prepared by allowing Compound (13) to react with Compound (14) in an inert solvent. As the inert solvent, ethyl acetate, acetone, diethylether, tetrahydrofuran, 1, 4-dioxane, 1, 2-dimethoxyethane, dichloromethane, 1, 2-dichloroethane, chloroform, N, N-dimethylformamide, N-methylpyrrolidone, dimethylsulfoxide, benzene, toluene, xylene, methanol, ethanol, 2-propanol, a mixed solvent thereof and the like can be illustrated. The reaction temperature is usually at 0° C. to reflux temperature, and the reaction time is usually from 30 minutes to 7 days, varying based on a used starting material, solvent and reaction temperature or the like.

Process 11

Indolizine compound (5) can be also prepared by allowing Compound (15) to react with acrylonitrile in an inert solvent in the presence of a base and manganese dioxide. As the inert solvent, benzene, toluene, xylene, diethylether, 1, 2-dimethoxyethane, dichloromethane, 1, 2-dichloroethane, chloroform, N, N-dimethyl-formamide, N-methylpyrrolidone, a mixed solvent thereof and the like can be illustrated. As the base, triethylamine, N, N-diisopropylethylamine, pyridine, 2, 6-lutidine, 1, 8-diazabicyclo[5, 4, 0]-7-undecene and the like can be illustrated. The reaction temperature is usually at 0° C. to reflux temperature, and the reaction time is usually from 30 minutes to 7 days, varying based on a used starting material, solvent and reaction temperature or the like.

Synthetic Method 6

[Chem. 13]

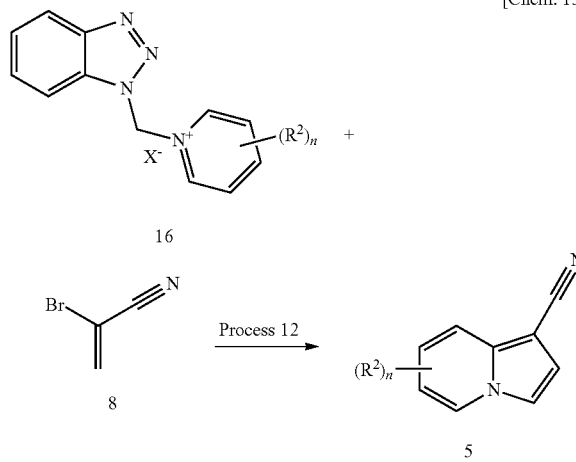

In the formula, $R^2$, n and X have the same meanings as defined above.

Process 12

Indolizine compound (5) can be also prepared by allowing Benzotriazole derivative (16) to react with 2-bromoacrylonitrile (8) by a method similar to the above Process 6.

Triazole compounds (7) and (16) used in the above synthetic methods can be also prepared by a method described in literature (for example, Katrizky, A. R, J. Org. Chem., 1999, 64, pp.7618-7621 or the like) or a similar method thereto and the like.

As the protective groups used in the present invention, various protective groups generally used in organic synthesis reaction can be used. For example, as the protective groups of a hydroxy group, in addition to a p-methoxybenzyl group, a benzyl group, a methoxymethyl group, an acetyl group, a pivaloyl group, a benzoyl group, a tert-butyldimethylsilyl group, a tert-butyldiphenylsilyl group, an allyl group and the like, when two hydroxy groups are adjacent, an isopropylidene group, a cyclopentylidene group, a cyclohexylidene group and the like can be illustrated. As the protective groups of a thiol group, a p-methoxybenzyl group, a benzyl group, an acetyl group, a pivaloyl group, a benzoyl group, a benzyloxycarbonyl group and the like can be illustrated. As the protective groups of an amino group, a benzyloxycarbonyl group, a tert-butoxycarbonyl group, a benzyl group, ap-methoxybenzyl group, a trifluoroacetyl group, an acetyl group, a phthaloyl group and the like can be illustrated. As the protective groups of a carboxy group, a $C_{1-6}$ alkyl group, a benzyl group, a tert-butyl-dimethylsilyl group, an allyl group and the like can be illustrated.

An indolizine derivative represented by the formula (I) of the present invention can be also isolated or purified by conventional isolation techniques, such as fractional recrystallization, purification by chromatography, solvent extraction, solid-phase extraction and the like.

An indolizine derivative represented by the formula (I) of the present invention can be also converted into pharmaceutically acceptable salts thereof in the usual way. As such a salt, an acid additive salt with a mineral acid such as hydrochloric acid, hydrobromic acid, hydroiodic acid, sulfuric acid, nitric acid, phosphoric acid and the like, an acid additive salt with an organic acid such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like, a salt with an inorganic base such as a sodium salt, a potassium salt, a calcium salt, a magnesium salt, a zinc salt, a lithium salt, an aluminum salt and the like, an additive salt with an organic base such as N-methyl-D-glucamine, N, N'-dibenzylethylenediamine, 2-aminoethanol, tris(hydroxymethyl)aminomethane, arginine, lysine, piperazine, choline, diethylamine, 4-phenylcyclohexane and the like can be illustrated.

Among the indolizine derivatives represented by the formula (I) of the present invention, in a compound having an unsaturated bond, there are two geometrical isomers, a compound of cis (Z) form and a compound of trans (E) form. In the present invention, either of the compounds can be employed, and a mixture thereof can be also employed.

Among the indolizine derivatives represented by the formula (I) of the present invention, in a compound having a chiral carbon atom, there are a compound of R configuration and a compound of S configuration for each chiral carbon. In the present invention, either of the optical isomers can be employed, and a mixture of the optical isomers thereof can be also employed.

In an indolizine derivative represented by the formula (I) of the present invention, there can be some tautomers, and the compounds of the present invention also include these tautomers.

In the present invention, the term "prodrug" means a compound to be converted into an indolizine derivative represented by the formula (I) within an organism. A prodrug of an indolizine derivative represented by the formula (I) of the present invention can be prepared by introducing an appropriate group forming a prodrug into any one or more groups selected from a hydroxy group, an amino group, a carboxy group and other groups which can form a prodrug of the compound represented by the formula (I) using a corresponding reagent to produce a prodrug such as a halide compound or the like in the usual way, and then by suitably isolating and purifying in the usual way as occasion demands. See *Gekkan-Yakuji iyakuhin tekiseisiyou no taineno rinsyou yakubutsudoutai* (monthly pharmaceutical, clinical pharmacokinetics for the proper use of pharmaceutical products), 2000.3. extra edition, Vol.42, No.4, pp.669-707, and *New Drug Delivery System*, published by CMC Co., Ltd., 2000.1.31., pp.67-173. As a group forming a prodrug used in a hydroxy group or an amino group, for example, $C_{1-6}$ alkyl-CO— such as acetyl, propionyl, butyryl, isobutyryl, pivaloyl and the like; aryl-CO— such as benzoyl and the like; $C_{1-6}$ alkyl-O—$C_{1-6}$ alkylene-CO—; $C_{1-6}$ alkyl-OCO—$C_{1-6}$ alkylene-CO—; $C_{1-6}$ alkyl-OCO— such as methyloxycarbonyl, ethyloxycarbonyl, propyloxycarbonyl, isopropyloxycarbonyl, Cert-butyloxycarbonyl and the like; $C_{1-6}$ alkyl-O—$C_{1-6}$ alkylene-OCO—; $C_{1-6}$ alkyl-COO—$C_{1-6}$ alkylene such as acetyloxymethyl, pivaloyloxymethyl, 1-(acetyloxy)ethyl, 1-(pivaloyloxy)ethyl and the like; $C_{1-6}$ alkyl-OCOO—$C_{1-6}$ alkylene such as methoxycarbonyloxymethyl, 1-(methoxycarbonyloxy)ethyl, ethoxycarbonyloxymethyl, 1-(ethoxycarbonyloxy)ethyl, isopropyloxycarbonyloxymethyl, 1-(isopropyloxycarbonyloxy)ethyl, Cert-butyloxycarbonyloxymethyl, 1-(cert-butyloxycarbonyloxy)ethyl and the like; $C_{3-8}$ cycloalkyl- OCOO—$C_{1-6}$ alkylene such as cyclohexyloxycarbonyloxymethyl, 1-(cyclohexyloxycarbonyl)ethyl and the like; an ester or an amide with an amino acid such as glycine and the like; and the like can be illustrated.

As a group forming a prodrug used in a carboxy group, for example, $C_{1-6}$ alkyl such as methyl, ethyl, propyl, isopropyl, butyl, tert-butyl and the like; $C_{1-6}$ alkyl-COO—$C_{1-6}$ alkylene such as pivaloyloxymethyl, acetyloxymethyl, 1-(pivaloyloxy)ethyl, 1-(acetyloxy)ethyl and the like; $C_{1-6}$ alkyl-OCOO—$C_{1-6}$ alkylene such as ethyloxy-carbonyloxymethyl, 1-(ethyloxycarbonyloxy)ethyl, isopropyloxycarbonyloxymethyl, 1-(isopropyloxycarbonyloxy)ethyl, tert-butyloxycarbonyloxymethyl, 1-(tert-butyloxy-carbonyloxy)ethyl and the like; $C_{3-8}$ cycloalkyl-OCOO—$C_{1-6}$ alkylene such as cyclohexyloxycarbonyloxymethyl, 1-(cyclohexyloxycarbonyloxy)ethyl and the like; mono(di)hydroxy $C_{1-6}$ alkyl such as hydroxyethyl, hydroxypropyl, 1, 2-dihydroxypropyl, 1-hydroxy-(2-hydroxymethyl)propyl and the like; mono(di)hydroxy $C_{1-6}$ alkyl-OCOO—$C_{1-6}$ alkylene such as 1-(hydroxyethyloxycarbonyloxy)ethyl and the like; $C_{1-6}$ alkoxy $C_{1-6}$ alkoxy $C_{1-6}$ alkyl such as methoxyethoxyethyl and the like; mono(di)$C_{1-6}$ alkylamino $C_{1-6}$ alkyl such as dimethylaminoethyl and the like; 3 to 8-membered heterocycloalkyl $C_{1-6}$ alkyl such as pyrrolidine-1-yl-ethyl and the like; $C_{1-6}$ alkyl-OCO-amino$C_{1-6}$ alkylene such as methyloxycarbonyl(amino)ethyl and the like; and the like can be illustrated.

As the prodrug of the present invention, a compound having a group forming the above prodrug in carboxy group is preferable. As the group forming such prodrug, mono(di)hydroxy $C_{1-6}$ alkyl such as hydroxyethyl, hydroxypropyl, 1, 2-dihydroxypropyl, 1-hydroxy-(2-hydroxymethyppropyl and the like; mono(di)hydroxy $C_{1-6}$ alkyl-OCOO—$C_{1-6}$ alkylene such as 1-(hydroxyethyloxycarbonyloxy)ethyl and the like; $C_{1-6}$ alkoxy $C_{1-6}$ alkoxy $C_{1-6}$ alkyl such as methoxyethoxyethyl and the like; mono(di)$C_{1-6}$ alkylamino $C_{1-6}$ alkyl such as dimcthylaminoethyl and the like; 3 to 8-membered heterocycloalkyl $C_{1-6}$ alkyl such as pyrrolidine- 1-yl-ethyl and the like; $C_{1-6}$ alkyl-OCO-arnino$C_{1-6}$ alkylene such as methyloxycarbonyl(amino)ethyl and the like; and the like is more preferable.

In the present invention, a pharmaceutically acceptable salt also includes a solvate thereof with a pharmaceutically acceptable solvent such as water, ethanol or the like.

A pharmaceutical composition of the present invention is useful for the prevention or treatment of diseases associated with high serum uric acid levels such as hyperuricemia, gouty tophus, gouty arthritis, renal disorder associated with hyperuricemia, urinary calculi or the like, especially for hyperuricemia.

When a pharmaceutical composition of the present invention are employed in the practical prevention or treatment, the dosage of a compound represented by the formula (1) or a prodrug thereof or a pharmaceutically acceptable salt thereof as the active ingredient is appropriately decided depending on the age, sex, body weight, degree of disorders and treatment of each patient and the like, for example, which is approximately within the range of from 1 to 2,000 mg per day per adult human in the case of oral administration, and the daily dose can be divided into one to several doses per day and administered.

When a pharmaceutical composition of the present invention are employed in the practical prevention or treatment, various dosage forms are orally or parenterally used depending on their uses, for example, formulations for oral administration such as powders, fine granules, granules, tablets, capsules, dry syrups or the like are preferable.

These pharmaceutical compositions can be prepared depending on their formulations optionally by admixing an appropriate pharmaceutical additive such as excipients, disintegrators, binders, lubricants and the like in accordance with conventional pharmaceutical methods, and formulating the mixture in accordance with conventional methods.

For example, powders can be formulated by, if desired, admixing well an active ingredient with appropriate excipients, lubricants and the like. For example, tablets can be formulated by tableting an active ingredient with appropriate excipients, disintegrators, binders, lubricants and the like in accordance with conventional methods, further if desired, can be suitably coated to provide film-coated tablets, sugar-coated tablets, enteric-coated tablets and the like. For example, capsules can be formulated by admixing well an active ingredient with appropriate excipients, lubricants and the like, or formulating fine granules or granules in accordance with conventional methods, and filling it in appropriate capsules. Furthermore, in the case of such an oral administration drug, it can be also formulated by conducting quick-release or sustained-release formulation depending on the prevention or the treatment methods.

An indolizine derivative represented by the formula (I) of the present invention or a prodrug thereof, or a pharmaceutically acceptable salt thereof can be also used further in combination with any other drug for the treatment of hyperuricemia or drug for the treatment of gout. As the drug for the treatment of hyperuricemia, for example, urinary alkalizers such as sodium hydrogen carbonate, potassium citrate, sodium citrate and the like, and the like can be also illustrated. In addition, as the drug for the treatment of gout, colchicine, or non-steroidal anti-inflammatory drugs such as indomethacin, naproxen, fenbufen, pranoprofen, oxaprozin, ketoprofen, etoricoxib, tenoxicam and the like and steroids and the like can be illustrated. When used in combination, not only a single pharmaceutical composition comprising together with the active ingredient of the present invention and the other active ingredient can be used but also pharmaceutical compositions which separately contain each active ingredient may be used for simultaneous administration or administration at different dosage intervals. Furthermore, the dosage of the indolizine derivative of the present invention can be reduced depending on the dosage of the other drug used in combination.

Effect of the Invention

The indolizine derivatives represented by the formula (1) of the present invention exert an excellent xanthine oxidase inhibitory activity and suppress the production of uric acid. A preferable compound of the present invention can also exert an excellent URAT1 inhibitory activity and enhance the uric acid excretion. Therefore, the indolizine derivatives represented by the formula (I) of the present invention or prodrugs thereof, or pharmaceutically acceptable salts thereof can extremely suppress the increase in scrum uric acid level and are useful as an agent for the prevention or treatment of diseases associated with abnormal serum uric acid level such as hyperuricemia or the like.

BEST MODE TO OPERATE THE INVENTION

The present invention is further illustrated in more detail by way of the following Reference Examples, Examples and Test Examples. However, the present invention is not limited thereto.

REFERENCE EXAMPLE 1

Indolizine-1-carbonitrile

To a solution of pyridine (4.0 g) in ethyl acetate (10 mL) was added chloroacetic acid (4.7 g) at room temperature, and the mixture was heated under reflux overnight. After the reaction mixture was cooled to room temperature, the precipitated solid was collected by filtration, and dried under reduced pressure to give 1-carboxymethyl pyridinium chloride (5.7 g). To a solution of the obtained compound (5.7 g) in toluene (300 mL) were added acrylonitrile (8.7 g), manganese dioxide (16.4 g) and triethylamine (4.0 g), and the mixture was stirred at 100° C. for 5 hours. The reaction mixture was filtered through a Celite pad, and the filtrate was concentrated under reduced pressure. The residue was purified by column chromatography on silica gel (eluent: n-hexane/ethyl acetate) to give the title compound (2.8 g).

REFERENCE EXAMPLES 2 TO 12

The compounds of Reference Examples 2 to 12 were prepared in a similar manner to that described in Reference Example 1 using the corresponding starting materials.

REFERENCE EXAMPLE 13

7-Trifluoromethylindolizine-1-carbonitrile

To a solution of 4-trifluoromethylpyridine (2.0 g) in ethyl acetate (10 mL) was added bromoacetic acid (1.4 g) at room temperature, and the mixture was heated under reflux overnight. After the reaction mixture was cooled to room temperature, the precipitated solid was collected by filtration, and dried under reduced pressure to give 1-carboxymethyl-4-trifluoromethylpyridinium bromide (1.0 g). To a solution of the obtained compound (1.0 g) in toluene (10 mL) were added acrylonitrile (0.93 g), manganese dioxide (0.91 g) and triethylamine (0.42 g), and the mixture was stirred at 100° C. for 5 hours. The reaction mixture was filtered through a Celite pad, and the filtrate was concentrated under reduced pressure. The residue was purified by column chromatography on silica gel (eluent: n-hexane/ethyl acetate) to give the title compound (0.31 g).

REFERENCE EXAMPLES 14 TO 16

The compounds of Reference Examples 14 to 16 were prepared in a similar manner to that described in Reference Example 13 using the corresponding starting materials.

REFERENCE EXAMPLE 17

The compound of Reference Example 17 was prepared in a similar manner to that described in Reference Example 1 using the corresponding starting material.

REFERENCE EXAMPLE 18

7-Hydroxymethylindolizine-1-carbonitrile

To a mixed solution of 1-cyanoindolizine-7-carboxylic acid ethyl ester (0.42 g) in tetrahydrofuran (4.2 mL), ethanol (2.1 mL) and water (2.1 mL) was added lithium hydroxide (0.25 g) at room temperature, and the mixture was stirred at the same temperature overnight. The reaction mixture was acidified with 2 mol/L hydrochloric acid, and a precipitated solid was collected by filtration. This solid was washed with water and n-hexane to give 1-cyanoindolizine-7-carboxylic acid (0.29 g).

To a solution of 1-cyanoindolizine-7-carboxylic acid (0.20 g) in tetrahydrofuran (4.0 mL) were added 3-methylbutyrylchloride (0.16 g) and 4-methylmorpholine (0.13 g) under ice-cooling, and the mixture was stirred at room temperature for 1 hour. The insoluble material was removed from the reaction mixture by filtration. To the filtrate was added ethanol (4.0 mL) and sodium borohydride (0.20 g) was added under ice-cooling, and the mixture was stirred at room temperature overnight. To the reaction mixture was added 2 mol/L hydrochloric acid (5.0 mL), and the resulting mixture was extracted with ethyl acetate. The organic layer was dried over magnesium sulfate, and concentrated. The residue was purified by column chromatography on silica gel (eluent: ethyl acetate/n-hexane=30/70-100/0) to give the title compound (0.050 g).

REFERENCE EXAMPLES 19 TO 31

The compounds of Reference Examples 19 to 31 were prepared in a similar manner to that described in Reference Example 13 using the corresponding starting materials.

REFERENCE EXAMPLE 32

7-Methoxyindolizine-1-carbonitrile

To a solution of 4-methoxypyridine (3.0 g) in ethyl acetate (30 mL) was added methyl bromoacetate (4.6 g), and the mixture was heated under reflux overnight. After cooling to room temperature, the precipitated solid was collected by filtration, and dried under reduced pressure to give 4-methoxy-1-methoxycarbonylmethylpyridinium bromide (7.0 g). To a solution of the obtained compound (6.0 g) in toluene (50 mL) were added acrylonitrile (6.1 g), manganese dioxide (6.0 g) and triethylamine (2.8 g), and the mixture was stirred at 100° C. for 5 hours. The reaction mixture was filtered through a Celite pad, and the filtrate was concentrated under reduced pressure. The residue was purified by column chromatography on silica gel (eluent: n-hexane/ethyl acetate) to give 1-cyano-7-methoxyindolizine-3-carboxylic acid methyl ester (1.0 g). To a mixed solution of the obtained compound (1.0 g) in tetrahydrofuran (20 mL), ethanol (7 mL) and water (7 mL) was added lithium hydroxide monohydrate (0.27 g), and the mixture was stirred at room temperature overnight. To the reaction mixture were added 1 mol/L hydrochloric acid and water, and the precipitated solid was collected by filtration, washed with water and n-hexane, and dried under reduced pressure at 50° C. to give the 1-cyano-7-methoxyindolizine-3-carboxylic acid (0.80 g). To a suspension of the obtained compound (0.80 g) and quinoline (8 mL) was added copper (0.05 g), and the mixture was stirred at 220° C. for 30 minutes. After cooling to room temperature, to the reaction mixture was added 1 mol/L hydrochloric acid, and the resulting mixture was extracted with ethyl acetate. The organic layer was washed with 1 mol/L hydrochloric acid, water and brine, dried over magnesium sulfate, and concentrated under reduced pressure. The residue was purified by column chromatography on silica gel (eluent: n-hexane/ethyl acetate) to give the title compound (0.37 g).

REFERENCE EXAMPLE 33

7-Dimethylaminoindolizine-1-carbonitrile

The compound of Reference Example 33 was prepared in a similar manner to that described in Reference Example 32 using the corresponding starting material.

REFERENCE EXAMPLE 34

7-Methoxy-6-methylindolizine-1-carbonitrile

The compound of Reference Example 34 was prepared in a similar manner to that described in Reference Example 32 using the corresponding starting material.

REFERENCE EXAMPLE 35

4-(1-Cyano-7-isopropoxy-8-trifluoromethylindolizine-3-yl) benzoic acid methyl ester To a solution of 4-chloro-3-trifluoromethylpyridine hydrochloride salt (2.0 g) in tetrahydrofuran (5 mL) were added sodium hydride (60%, 2.8 g) and propan-2-ol (2.8 g), and the mixture was stirred at 50° C. for 2 hours. After cooling to room temperature, to the reaction mixture was added water, and the resulting mixture was extracted with diethyl ether. The organic layer was dried over magnesium sulfate, and concentrated. The residue was purified by column chromatography on silica gel (eluent: n-hexane/ethyl acetate) to give 4-isopropoxy-3-trifluoromethylpyridine (1.5 g). To a solution of the obtained compound (1.5 g) in ethyl acetate (20 mL) was added 4-bromomethylbenzoic acid methyl ester (2.0 g) at room temperature, and the mixture was heated under reflux overnight. After cooling to room temperature, the solvent was removed to give 4-isopropoxy-1-(4-methoxycarbonylbenzyl)-3-trifluoromethyl-pyridinium bromide (2.1 g). To a solution of the obtained compound (2.1 g) in dimethoxyethane (10 mL) were added acrylonitrile (1.3 g), manganese dioxide (2.1 g) and triethylamine (1.5 g), and the mixture was stirred at 80° C. for 6 hours. The reaction mixture was filtered through a Celite pad, and filtrate was concentrated under reduced pressure. The residue was purified by column chromatography on silica gel (eluent: n-hexane/ethyl acetate) to give the title compound (0.04 g).

REFERENCE EXAMPLE 36

1-Bromo-2-fluoroindolizine

To a solution of 1-ethoxycarbonylmethylpyridinium bromide (4.8 g) in N, N-dimethylformamide (50 mL) were added toluene-4-sulfonic acid 2, 2-difluorovinyl ester (4.6 g), potassium carbonate (4.0 g) and triethylamine (3.0 g), and the mixture was stirred at 70° C. overnight. After cooling to room temperature, to the reaction mixture was added water, and the resulting mixture was extracted with ethyl acetate. The organic layer was washed with water and brine, dried over magnesium sulfate, and concentrated under reduced pressure. The residue was purified by column chromatography on silica gel (eluent: n-hexane/ethyl acetate) to give 2-fluoroindolizine-3-carboxylic acid ethyl ester (1.9 g). To a solution of the obtained. compound (1.9 g) in dichloromethane (30 mL) was added N-bromosuccinimide (1.8 g), and the mixture was stirred at room temperature for 2 hours. To the reaction mixture was added 1 mol/L sodium thiosulfate aqueous solution, and the resulting mixture was extracted with dichloromethane. The organic layer was washed with water and brine, dried over magnesium sulfate, and concentrated under reduced pressure. The residue was purified by column chromatography on silica gel (eluent: n-hexane/ethyl acetate) to give 1-bromo-2-fluoroindolizine-3-carboxylic acid ethyl ester (1.3 g). To a mixed solution of the obtained compound (1.3 g) in tetrahydrofuran (20 mL), ethanol (7 mL) and water (7 mL) was added lithium hydroxide monohydrate (0.29 g), and the mixture was stirred at room temperature overnight. To the reaction mixture were added 1 mol/L hydrochloric acid and water. The precipitated solid was collected by filtration, washed with water and n-hexane, and dried under reduced pressure at 50° C. to give 1-bromo-2-fluoroindolizine-3-carboxylic acid (0.76 g). To a suspension of the obtained compound (0.56 g) and quinoline (5 mL) was added copper (0.03 g), and the mixture was stirred at 220° C. for 30 minutes. After cooling to room temperature, to the reaction mixture was added 1 mol/L hydrochloric acid, and the resulting mixture was extracted with ethyl acetate. The organic layer was washed with 1 mol/L hydrochloric acid, water and brine, dried over magnesium sulfate, and concentrated under reduced pressure. The residue was purified by column chromatography on silica gel (eluent: n-hexane/ethyl acetate) to give the title compound (0.47 g).

REFERENCE EXAMPLE 37

5-Bromo-3-methoxymethoxypyridine-2-carboxylic acid ethyl ester

To a solution of 5-bromo-3-hydroxypridine-2-carboxylic acid (2.18 g) in ethanol (20 mL) was added thionyl chloride (4.76 g) under ice-cooling, and the mixture was stirred at 80° C. for 24 hours. After cooling to room temperature, the solvent was removed. To a solution of the obtained compound (2.05 g) and diisopropylethylamine (5.38 g) in dichloromethane (17 mL) was added dropwise chloromethoxymethane (2.01 g) under ice-cooling, and the mixture was stirred at room temperature for 4 hours. To the reaction mixture were added hydrochloric acid and water, and the resulting mixture was extracted with ethyl acetate. The organic layer was dried over magnesium sulfate, and concentrated under reduced pressure. The residue was purified by column chromatography on silica gel (eluent: n-hexane/ethyl acetate) to give the title compound (2.26 g).

EXAMPLE 1

4-(1-Cyanoindolizine-3-yl) benzoic acid

To a solution of indolizine-1-carbonitrile (0.80 g) in N-methylpyrrolidone (16 mL) were added methyl 4-iodobenzoate (1.60 g), dichlorobis (triphenylphosphinc) palladium (II) (0.20 g), potassium acetate (1.10 g) and water (0.2 mL), and the mixture was stirred at 100° C. for 3 hours. After cooling to room temperature, to the reaction mixture was added water, and the resulting mixture was extracted with ethyl acetate. The organic layer was washed with water and brine, dried over magnesium sulfate, and concentrated under reduced pressure. The residue was purified by column chromatography on silica gel (eluent: n-hexane/ethyl acetate=100/0-34/66) to give methyl 4-(1-cyanoindolizine-3-yl) benzoate (0.45 g). To a mixed solution of the obtained compound (0.45 g) in tetrahydrofuran (10 mL), ethanol (5 mL) and water (5 mL) was added lithium hydroxide monohydrate (0.20 g), and the mixture was stirred at room temperature overnight. To the reaction mixture were added 1 mol/L hydrochloric acid and water, and the precipitated solid was collected by filtration, washed with water and n-hexane, and dried under reduced pressure at 50° C. to give the title compound (0.42 g).

EXAMPLES 2 TO 16

The compounds of Examples 2 to 16 were prepared in a similar manner to that described in Example 1 using the corresponding starting materials.

EXAMPLE 17

4-(1-Cyanoindolizine-3-yl)-2-hydroxybenzoic acid

To a solution of indolizine-1-carbonitrile (0.20 g) in N-methylpyrrolidone (5 mL) were added methyl 4-iodo-2-methoxymethoxybenzoate (0.5 g), dichlorobis (triphenylphosphine) palladium (II) (0.05 g), potassium acetate (0.28 g) and water (0.05 mL), and the mixture was stirred at 100° C. for 1 hour. After cooling to room temperature, to the reaction mixture was added water, and the resulting mixture was extracted with ethyl acetate. The organic layer was washed with water and brine, dried over magnesium sulfate, and concentrated under reduced pressure. The residue was purified by column chromatography on silica gel (eluent: n-hexane/ethyl acetate=100/0-0/100) to give methyl 4-(1-cyanoindolizine-3-yl)-2-methoxymethoxybenzoate (0.17 g). To a mixed solution of the obtained compound (0.17 g) in tetrahydrofuran (4.5 mL), ethanol (1.5 mL) and water (1.5 mL) was added lithium hydroxide monohydrate (0.10 g), and the mixture was stirred at room temperature overnight. To the reaction mixture was added 2 mol/L hydrochloric acid (1.5 mL), and the mixture was stirred at 50° C. overnight. After cooling to room temperature, to the reaction mixture was added water. The precipitated solid was collected by filtration, washed with water and n-hexane, and dried under reduced pressure at 50° C. to give the title compound (0.11 g).

EXAMPLES 18 TO 27

The compounds of Examples 18 to 27 were prepared in a similar manner to that described in Example 17 using the corresponding starting materials.

EXAMPLES 28, 29

The compounds of Examples 28 and 29 were prepared in a similar manner to that described in Example 1 using the corresponding starting materials.

EXAMPLE 30

2-Amino-4-(1-cyanoindolizine-3-yl) benzoic acid

Ethyl 4-(1-cyanoindolizine-3-yl)-2-nitrobenzoate (0.13 g) was prepared in a similar manner to that described in Example 1 using the corresponding starting material. To a solution of the obtained compound (0.13 g) in ethyl acetate (10 mL) was added palladium-carbon powder (0.02 g), and the mixture was stirred under a hydrogen atmosphere at room temperature overnight. The insoluble material was removed from the mixture by filtration, and the filtrate was concentrated under reduced pressure. The residue was purified by column chromatography on silica gel (eluent: n-hexane/ethyl acetate=100/0-0/100) to give ethyl 2-amino-4-(1-cyanoindolizine-3-yl) benzoate (0.02 g). To a mixed solution of the obtained compound (0.02 g) in tetrahydrofuran (0.6 mL), ethanol (0.2 mL) and water (0.2 mL) was added lithium hydroxide monohydrate (0.01 g), and the mixture was stirred at room temperature overnight. To the reaction mixture were added 1 mol/L hydrochloric acid and water, the precipitated solid was collected by filtration, washed with water and n-hexane, and dried under reduced pressure at 50° C. to give the title compound (0.01 g).

EXAMPLE 31

4-(1-Cyano-7-fluoromethylindolizine-3-yl) benzoic acid

To a solution of 7-hydroxymethylindolizine-1-carbonitrile (0.05 g) in N-methylpyrrolidone (2.0 mL) were added methyl 4-bromobenzoate (0.031 g), dichlorobis (triphenylphosphine) palladium (0.005 g), water (0.005 g) and potassium acetate (0.029 g), and the mixture was stirred at 100° C. for 2 hours. After cooling to room temperature, to the mixture were added acetone, ethyl acetate and water, and the two-layers were separated. The organic layer was washed with water, and concentrated. The residue was purified by column chromatography on silica gel (eluent: ethyl acetate/n-hexane=10/90-80/20). The obtained solid was washed with diethyl ether to give methyl 4-(1-cyano-7-hydroxymethylindolizine-3-yl) benzoate (0.026 g). To a suspension of the obtained compound (0.025 g) in dichloromethane (2.0 mL) was added N,N-diethylaminosulfur trifluoride (0.036 g) under ice-cooling, and the mixture was stirred at the same temperature for 1 hour. To the reaction mixture was added saturated sodium hydrogen carbonate aqueous solution, and the resulting mixture was extracted with diethyl ether. The organic layer was washed with water, dried over magnesium sulfate, and concentrated. The residue was purified by column chromatography on silica gel (eluent: ethyl acetate/n-hexane) to give methyl 4-(1-cyano-7-fluoromethylindolizine-3-yl) benzoate (0.021 g). To a mixed solution of the obtained compound (0.021 g) in tetrahydrofuran (1.0 mL), ethanol (0.5 mL) and water (0.5 mL) was added lithium hydroxide (0.008 g) at room temperature, and the mixture was stirred at the same temperature overnight. The reaction mixture was acidified with 2 mol/L hydrochloric acid, and the resulting mixture was extracted with ethyl acetate. The organic layer was washed with water, dried over magnesium sulfate, and concentrated to give the title compound (0.005 g).

EXAMPLE 32

The compound of Example 32 was prepared in a similar manner to that described in Example 1 using the corresponding starting material.

EXAMPLES 33 TO 34

The compounds of Examples 33 to 34 were prepared in a similar manner to that described in Example 1 using the corresponding starting materials.

EXAMPLE 35

The compound of Example 35 was prepared in a similar manner to that described in Example 1 using methyl 4-bromo-2-methybenzoate instead of methyl 4-iodobenzoate.

EXAMPLES 36 TO 46

The compounds of Examples 36 to 46 were prepared in a similar manner to that described in Example 1 using the corresponding starting materials.

EXAMPLE 47

4-(1-Cyano-7-isopropoxy-8-trifluoromethylindolizine-3-yl) benzoic acid

To a mixed solution of methyl 4-(1-cyano-7-isopropoxy-8-trifluoromethyl-indolizine-3-yl) benzoate (0.04 g) in tetrahydrofuran (2 mL), ethanol (1 mL) and water (1 mL) was added lithium hydroxide monohydrate (0.01 g), and the mixture was stirred at room temperature overnight. To the reaction mixture was added 1 mol/L hydrochloric acid and water, and the precipitated solid was collected by filtration, washed with water and n-hexane, and dried under reduced pressure at 50° C. to give the title compound (0.02 g).

EXAMPLES 48 TO 60

The compounds of Examples 48 to 60 were prepared in a similar manner to that described in Example 17 using the corresponding starting materials.

EXAMPLE 61

4-(1-Cyano-2-fluoroindolizine-3-yl) benzoic acid

To a solution of 1-bromo-2-fluoroindolizine (0.15 g) in N-methylpyrrolidone (2.5 mL) were added methyl 4-bromobenzoate (0.18 g), dichlorobis (triphenylphosphine) palladium (II) (0.02 g), potassium acetate (0.13 g) and water (0.03 mL), and the mixture was stirred at 100° C. for 3 hours. After cooling to room temperature, to the reaction mixture was added water, and the resulting mixture was extracted with ethyl acetate. The organic layer was washed with water and brine, dried over magnesium sulfate, and concentrated under reduced pressure. The residue was purified by column chromatography on silica gel (eluent: n-hexane/ethyl acetate) to give methyl 4-(1-bromo-2-fluoroindolizine-3-yl) benzoate (0.17 g). To a solution of the obtained compound (0.17 g) in N-methylpyrrolidone (2 mL) were added zinc cyanide (0.23 g) and tetrakis (triphenylphosphine) palladium (0.21 g), and the mixture was stirred at 150° C. for 1 hour using microwave reactor. To the reaction mixture was added water, and the resulting mixture was extracted with ethyl acetate. The organic layer was washed with water and brine, dried over magnesium sulfate, and concentrated under reduced pressure. The residue was washed with diethyl ether to give methyl 4-(1-cyano-2-fluoroindolizine-3-yl) benzoate (0.10 g). To a mixed solution of the obtained compound (0.10 g) in tetrahydrofuran (4.0 mL), ethanol (1.5 mL) and water (1.5 mL) was added lithium hydroxide monohydrate (0.07 g), and the mixture was stirred at room temperature overnight. To the reaction mixture were added 1 mol/L hydrochloric acid and water, the precipitated solid was collected by filtration, washed with water and methanol, and dried under reduced pressure at 50° C. to give the title compound (0.07 g).

EXAMPLE 62

4-(1-Cyano-2-fluoroindolizine-3-yl)-2-hydroxybenzoic acid

To a solution of 1-bromo-2-fluoroindolizine (0.30 g) in N-methylpyrrolidone (6.0 mL) were added methyl 4-iodo-2-methoxymethoxybenzoate (0.54 g), dichlorobis (triphenylphosphine) palladium (II) (0.05 g), potassium acetate (0.27 g) and water (0.05 mL), and the mixture was stirred at 100° C. for 5 hours. After cooling to room temperature, to the reaction mixture was added water, and the resulting mixture was extracted with ethyl acetate. The organic layer was washed with water and brine, dried over magnesium sulfate, and concentrated under reduced pressure. The residue was purified by column chromatography on silica gel (eluent: n-hexane/ethyl acetate) to give methyl 4-(1-bromo-2-fluoroindolizine-3-yl)-2-methoxymethoxybenzoate (0.39 g). To a solution of the obtained compound (0.39 g) in N-methylpyrrolidone (3 mL) were added zinc cyanide (0.44 g) and tetrakis (triphenylphosphine) palladium (0.22 g), and stirred at 150° C. for 1 hour using microwave reactor. To the reaction mixture was added water, and the resulting mixture was extracted with ethyl acetate. The organic layer was washed with water and brine, dried over magnesium sulfate, and concentrated under reduced pressure. The residue was washed with diethyl ether to give methyl 4-(1-cyano-2-fluoroindolizine-3-yl)-2-methoxymethoxybenzoate (0.07 g). To a mixed solution of the obtained compound (0.07 g) in tetrahydrofuran (3.0 mL), ethanol (1.0 mL) and water (1.0 mL) was added lithium hydroxide monohydrate (0.04 g), and the mixture was stirred at room temperature overnight. To the reaction mixture was added 2 mol/L hydrochloric acid (1.0 mL), and the mixture was stirred at 50° C. overnight. After cooling to room temperature, to the reaction mixture was added water. The precipitated solid was collected by filtration, washed with water and methanol, and dried under reduced pressure at 50° C. to give the title compound (0.05 g).

EXAMPLE 63

4-(1-Cyano-7-fluoromethylindolizine-3-yl)-2-hydroxybenzoic acid

The compound of Example 63 was prepared in a similar manner to that described in Example 31 using the corresponding starting material.

EXAMPLE 64

The compound of Example 64 was prepared in a similar manner to that described in Example 1 using the corresponding starting material.

EXAMPLES 65 TO 67

The compounds of Examples 65 to 67 were prepared in a similar manner to that described in Example 17 using 5-bromo-3-methoxymethoxypyridine-2-carboxylic acid ethyl ester instead of 4-iodo-2-methoxymethoxybenzoic acid.

EXAMPLES 68 TO 71

The compounds of Examples 68 to 71 were prepared in a similar manner to that described in Example 1 using the corresponding starting materials.

EXAMPLES 72 TO 73

The compounds of Examples 72 to 73 were prepared in a similar manner to that described in Example 1 using the corresponding starting materials.

Tables 1 to 16 show the chemical structures and $^1$H-NMR data of the above compounds of Reference Examples 1 to 37 and Examples 1 to 73.

The abbreviations in these Tables: "Ref No.", "Ex No.", "Str." and "Solv.", represent Reference Example number, Example number, chemical structure and measurement solvent of $^1$H-NMR, respectively.

TABLE 1

| Ref No. | Str. | (Solv) $^1$H-NMR δ ppm |
|---|---|---|
| 1 | | (CDCl$_3$) 6.70-6.80 (1H, m), 7.0-7.15 (2H, m), 7.20-7.30 (1H, m), 7.60-7.70 (1H, m), 7.95-8.05 (1H, m) |
| 2 | | (DMSO-d6) 2.35 (3H, s), 6.70-6.80 (1H, m), 7.10 (1H, d, J = 3.0 Hz), 7.40-7.45 (1H, m), 7.58 (1H, d, J = 3.0 Hz), 8.41 (1H, d, J = 3.0 Hz) |
| 3 | | (CDCl$_3$) 6.69 (1H, t, J = 7.2 Hz), 7.00-7.15 (2H, m), 7.31 (1H, d, J = 3.0 Hz), 7.90-8.00 (1H, m) |
| 4 | | (DMSO-d6) 2.60 (3H, s), 6.75-7.00 (2H, m), 7.17 (1H, d, J = 3.0 Hz), 7.66 (1H, d, J = 3.0 Hz), 8.30-8.45 (1H, m) |
| 5 | | (DMSO-d6) 2.26 (3H, s), 7.00-7.20 (2H, m), 7.50-7.65 (2H, m), 8.30-8.35 (1H, m) |
| 6 | | (CDCl$_3$) 2.24 (3H, s), 2.68 (3H, s), 6.64 (1H, s), 6.96 (1H, d, J = 3.0 Hz), 7.12 (1H, d, J = 3.0 Hz), 7.67 (1H, s) |
| 7 | | (DMSO-d6) 2.20-2.35 (3H, m), 6.70-7.25 (2H, m), 7.65-8.40 (2H, m) |

TABLE 1-continued

| Ref No. | Str. | (Solv) $^1$H-NMR δ ppm |
|---|---|---|
| 8 | | (DMSO-d6) 2.25-2.40 (3H, m), 7.10-7.65 (3H, m), 8.65-8.80 (1H, m) |
| 9 | | (DMSO-d6) 1.50-2.00 (4H, m), 2.60-3.10 (4H, m), 6.60 (1H, d, J = 7.0 Hz), 7.06 (1H, d, J = 3.0 Hz), 7.54 (1H, d, J = 3.0 Hz), 8.24 (1H, d, J = 7.0 Hz) |

TABLE 2

| Ref No. | Str. | (Solv) $^1$H-NMR δ ppm |
|---|---|---|
| 10 | | (CDCl$_3$) 1.28 (3H, t, J = 7.6 Hz), 2.60-2.75 (2H, m), 6.55-6.65 (1H, m), 6.96 (1H, d, J = 3.0 Hz), 7.15 (1H, d, J = 3.0 Hz), 7.35-7.45 (1H, m), 7.85-7.95 (1H, m) |
| 11 | | (DMSO-d6) 1.27 (3H, t, J = 7.6 Hz), 2.98 (2H, q, J = 7.6 Hz), 6.75-7.25 (3H, m), 7.60-8.50 (2H, m) |
| 12 | | (DMSO-d6) 1.19 (3H, t, J = 7.6 Hz), 2.58 (2H, q, J = 7.6 Hz), 7.00-7.20 (2H, m), 7.50-7.65 (2H, m), 8.30-8.45 (1H, m) |
| 13 | | (DMSO-d6) 7.00-7.55 (2H, m), 7.80-8.85 (3H, m) |
| 14 | | (DMSO-d6) 6.85-6.95 (1H, m), 7.00-7.15 (1H, m), 7.28 (1H, d, J = 3.0 Hz), 7.80-7.90 (1H, m), 8.35-8.45 (1H, m) |
| 15 | | (DMSO-d6) 7.20-7.35 (2H, m), 7.65-7.80 (2H, m), 8.75-8.80 (1H, m) |

TABLE 2-continued

| Ref No. | Str. | (Solv) ¹H-NMR δ ppm |
|---|---|---|
| 16 | | (DMSO-d6) 2.34 (3H, s), 2.57 (3H, s), 6.60-6.80 (1H, m), 7.10-7.55 (3H, m) |
| 17 | | (DMSO-d6) 1.38 (3H, t, J = 7.2 Hz), 4.36 (2H, q, J = 7.2 Hz), 7.30 (1H, dd, J = 7.3 Hz, 1.7 Hz), 7.41 (1H, d, J = 2.9 Hz), 7.90-7.95 (1H, m), 8.15-8.20 (1H, m), 8.55-8.65 (1H, m) |
| 18 | | (DMSO-d6) 4.50-4.60 (2H, m), 5.44 (1H, t, J = 5.8 Hz), 6.80-6.95 (1H, m), 7.10-7.15 (1H, m), 7.50-7.55 (1H, m), 7.60-7.65 (1H, m), 8.40-8.50 (1H, m) |

TABLE 3

| Ref No. | Str. | (Solv) ¹H-NMR δ ppm |
|---|---|---|
| 19 | | (DMSO-d6) 2.38 (3H, s), 7.18 (1H, d, J = 3.0 Hz), 7.58 (1H, d, J = 3.0 Hz), 7.67 (1H, s), 8.83 (1H, s) |
| 20 | | (DMSO-d6) 2.37 (3H, s), 6.90 (1H, d, J = 7.1 Hz), 7.21 (1H, d, J = 3.0 Hz), 7.70 (1H, d, J = 3.0 Hz), 8.43 (1H, d, J = 7.1 Hz) |
| 21 | | (DMSO-d6) 7.25-7.55 (2H, m), 7.75-7.90 (1H, m), 8.65-8.80 (1H, m) |
| 22 | | (DMSO-d6) 3.94 (3H, s), 6.50-6.90 (2H, m), 7.00-7.20 (1H, m), 7.55-7.75 (1H, m), 8.00-8.20 (1H, m) |
| 23 | | (DMSO-d6) 1.23 (6H, d, J = 6.9 Hz), 2.85-3.05 (1H, m), 6.80-7.65 (4H, m), 8.35-8.55 1H, m) |
| 24 | | (DMSO-d6) 1.31 (9H, s), 6.95-7.20 (2H, m), 7.30-7.65 (2H, m), 8.35-8.55 (1H, m) |
| 25 | | (DMSO-d6) 1.45 (6H, s), 5.29 (1H, s), 6.90-7.20 (2H, m), 7.50-7.70 (2H, m), 8.35-8.55 (1H, m) |
| 26 | | (DMSO-d6) 7.15-7.35 (2H, m), 7.65-8.00 (3H, m), 8.45-8.70 (2H, m) |
| 27 | | (DMSO-d6) 2.66 (3H, s), 6.97 (1H, d, J = 7.3 Hz), 7.22 (1H, d, J = 3.1 Hz), 7.69 (1H, d, J = 3.1 Hz), 8.41 (1H, d, J = 7.3 Hz) |

TABLE 4

| Ref No. | Str. | (Solv) ¹H-NMR δ ppm |
|---|---|---|
| 28 | 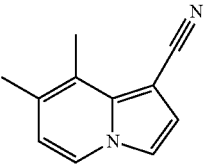 | (DMSO-d6) 2.27 (3H, s), 2.54 (3H, s), 7.10 (1H, d, J = 3.0 Hz), 7.45 (1H, d, J = 7.0 Hz), 7.58 (1H, d, J = 3.0 Hz), 8.28 (1H, d, J = 7.0 Hz) |

TABLE 4-continued

| Ref No. | Str. | (Solv) $^1$H-NMR δ ppm |
|---|---|---|
| 29 | | (DMSO-d6) 7.47 (1H, d, J = 3.0 Hz), 7.90 (1H, d, J = 3.0 Hz), 8.05-8.25 (1H, m), 8.90-9.15 (1H, m) |
| 30 | | (DMS-d6) 2.66 (3H, s), 7.20-7.45 (2H, m), 7.85-8.65 (3H, m) |
| 31 | | (DMSO-d6) 7.10-7.25 (1H, m), 7.46 (1H, d, J = 3.0 Hz), 7.94 (1H, d, J = 3.0 Hz), 8.35-8.70 (2H, m) |
| 32 | | (DMSO-d6) 3.87 (3H, s), 6.55-7.10 (3H, m), 7.35-7.55 (1H, m), 8.30-8.50 (1H, m) |
| 34 | | (DMSO-d6) 2.10 (3H, s), 3.90 (3H, s), 6.88 (1H, s), 6.96 (1H, d, J = 3.0 Hz), 7.35 (1H, d, J = 3.0 Hz), 8.28 (1H, s) |
| 35 | | (DMSO-d6) 1.20-1.45 (6H, m), 3.90 (3H, s), 4.80-5.10 (1H, m), 7.00-8.80 (7H, m) |
| 36 | | (DMSO-d6) 6.60-7.05 (2H, m), 7.20-7.40 (1H, m), 7.65-7.85 (1H, m), 8.15-8.35 (1H, m) |

TABLE 5

| Ref No. | Str. | (Solv) $^1$H-NMR δ ppm |
|---|---|---|
| 37 | (5-bromo-3-(methoxymethoxy)pyridine-2-carboxylic acid ethyl ester) | (DMSO-d6) 1.29 (3H, t, J = 7.2 Hz), 3.39 (3H, s), 4.32 (2H, q, J = 7.2 Hz), 5.37 (2H, s), 8.01 (1H, d, J = 1.7 Hz), 8.39 (1H, d, J = 1.7 Hz) |

TABLE 6

| Ex No. | Str. | $^1$H-NMR δ ppm (DMSO-d6) |
|---|---|---|
| 1 | | 6.95-7.05 (1H, m), 7.25-7.35 (1H, m), 7.53 (1H, s), 7.65-7.90 (3H, m), 8.08 (2H, d, J = 8.2 Hz), 8.64 (1H, d, J = 7.3 Hz), 13.1 (1H, brs.) |
| 2 | | 2.40 (3H, s), 6.86 (1H, dd, J = 7.3 Hz, 1.8 Hz,), 7.45 (1H, s), 7.50-7.60 (1H, m), 7.70-7.80 (2H, m), 8.00-8.15 (2H, m), 8.56 (1H, d, J = 7.3 Hz), 13.1 (1H, brs.) |
| 3 | | 6.96 (1H, t, J = 7.2 Hz), 7.44 (1H, d, J = 7.4 Hz), 7.61 (1H, s), 7.78 (2H, d, J = 8.2 Hz), 8.09 (2H, d, J = 8.2 Hz), 8.56 (1H, d, J = 7.1 Hz) |
| 4 | | 2.68 (3H, s), 6.80-7.15 (2H, m), 7.48 (1H, s), 7.70-8.50 (5H, m), 13.14 (1H, brs.) |

TABLE 6-continued

| Ex No. | Str. | ¹H-NMR δ ppm (DMSO-d6) |
|---|---|---|
| 5 | (structure) | 2.29 (3H, s), 7.10-7.30 (1H, m), 7.45 (1H, s), 7.60-8.60 (6H, m), 13.12 (1H, brs.) |
| 6 | (structure) | 2.24 (3H, s), 2.64 (3H, s), 6.95 (1H, s), 7.41 (1H, s), 7.75 (2H, d, J = 8.2 Hz), 8.08 (2H, d, J = 8.2 Hz), 8.20-8.30 (1H, s), 13.1 (1H, brs.) |
| 7 | (structure) | 2.32 (3H, d, J = 2.0 Hz), 6.89 (1H, t, J = 7.2 Hz), 7.52 (1H, s), 7.70-8.15 (4H, m), 8.39 (1H, d, J = 7.2 Hz), 13.18 (1H, brs.) |

TABLE 7

| Ex No. | Str. | ¹H-NMR δ ppm (DMSO-d6) |
|---|---|---|
| 8 | (structure) | 2.37 (3H, s), 7.51 (1H, s), 7.65-8.80 (6H, m), 13.11 (1H, brs.) |
| 9 | (structure) | 1.65-2.00 (4H, m), 2.65-3.20 (4H, m), 6.71 (1H, d, J = 7.3 Hz), 7.39 (1H, s), 7.65-8.15 (4H, m), 8.35 (1H, d, J = 7.3 Hz), 13.10 (1H, brs.) |

TABLE 7-continued

| Ex No. | Str. | ¹H-NMR δ ppm (DMSO-d6) |
|---|---|---|
| 10 | | 1.24 (3H, t, J = 7.6 Hz), 2.71 (2H, q, J = 7.6 Hz), 6.85-7.00 (1H, m), 7.46 (1H, s), 7.50-7.55 (1H, m), 7.70-7.85 (2H, m), 8.05-8.10 (2H, m), 8.57 (1H, m), 13.1 (1H, brs.) |
| 11 | | 1.31 (3H, t, J = 7.4), 3.08 (2H, q, J = 7.4 Hz), 6.80-7.20 (2H, m), 7.49 (1H, s), 7.65-8.60 (5H, m), 13.14 (1H, brs) |
| 12 | | 1.19 (3H, t, J = 7.4 Hz), 2.62 (2H, q, J = 7.4 Hz), 7.15-7.35 (1H, m), 7.46 (1H, s), 7.60-8.50 (6H, m) |
| 13 | | 6.85-7.30 (2H, m), 7.59 (1H, s), 7.79 (2H, d, J = 8.1 Hz), 8.10 (2H, d, J = 8.1 Hz), 8.46 (1H, d, J = 6.9 Hz), 13.2 (1H, brs.) |
| 14 | | 6.90-7.05 (1H, m), 7.10-7.30 (1H, m), 7.59 (1H, s), 7.79 (2H, d, J = 7.8 Hz), 8.10 (2H, d, J = 7.8 Hz), 8.46 (1H, d, J = 6.8 Hz), 13.2 (1H, brs.) |

TABLE 8
| Ex No. | Str. | ¹H-NMR δ ppm (DMSO-d6) |
|---|---|---|
| 15 | 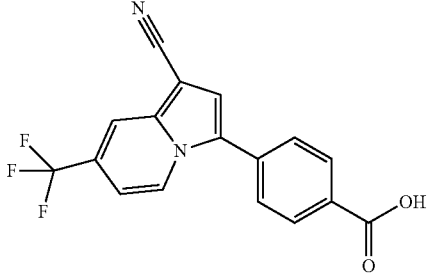 [SMILES: N#Cc1cc(-c2ccc(C(=O)O)cc2)n2ccc(C(F)(F)F)cc12] | 7.05-7.25 (1H, m), 7.74 (1H, s), 7.80-8.25 (5H, m), 8.65-8.85 (1H, m), 13.21 (1H, brs.) |
| 16 | 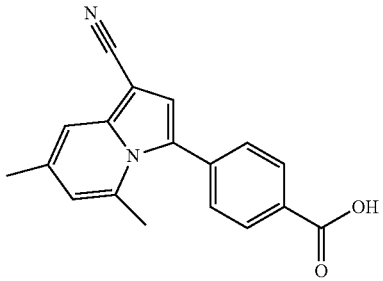 [SMILES: Cc1cc(C)n2c(-c3ccc(C(=O)O)cc3)cc(C#N)c2c1] | 2.08 (3H, s), 2.35 (3H, s), 6.55-6.75 (1H, m), 7.18 (1H, s), 7.35-8.05 (5H, m), 13.13 (1H, brs.) |
| 17 | 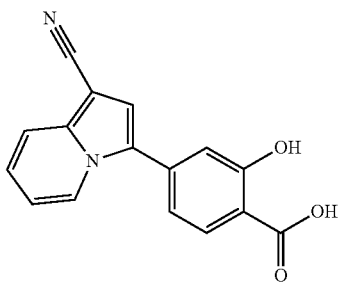 [SMILES: N#Cc1cc(-c2ccc(C(=O)O)c(O)c2)n2ccccc12] | 6.90-7.40 (4H, m), 7.53 (1H, s), 7.70-8.00 (2H, m), 8.55-8.70 (1H, m) |
| 18 | 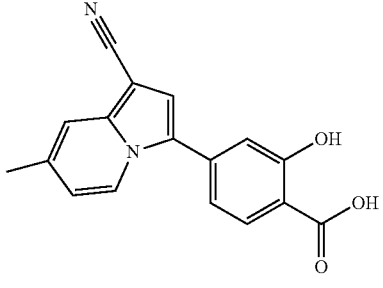 [SMILES: Cc1ccn2c(-c3ccc(C(=O)O)c(O)c3)cc(C#N)c2c1] | 2.40 (3H, s), 6.80-7.60 (5H, m), 7.80-8.65 (2H, m) |
| 19 | 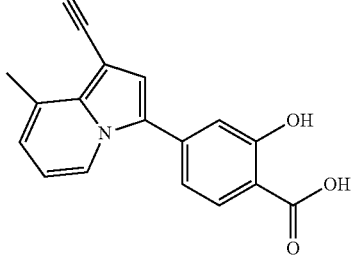 | 2.67 (3H, s), 6.85-7.25 (4H, m), 7.49 (1H, s), 7.85-8.55 (2H, m) |

TABLE 8-continued

| Ex No. | Str. | $^1$H-NMR δ ppm (DMSO-d6) |
| --- | --- | --- |
| 20 | | 2.30 (3H, s), 7.10-7.30 (3H, m), 7.45 (1H, s), 7.60-8.50 (3H, m) |
| 21 | | 2.24 (3H, s), 2.64 (3H, s), 6.95 (1H, s), 7.10-7.25 (2H, m), 7.42 (1H, s), 7.85-7.95 (1H, m), 8.26 (1H, s), |

TABLE 9

| Ex No. | Str. | $^1$H-NMR δ ppm (DMSO-d6) |
| --- | --- | --- |
| 22 | | 2.37 (3H, s), 7.15-7.30 (2H, m), 7.52 (1H, s), 7.70-7.95 (2H, m), 8.60-8.80 (1H, m) |
| 23 | | 2.32 (3H, d, J = 2.1 Hz), 6.80-7.25 (3H, m), 7.52 (1H, s), 7.85-8.50 (2H, m) |
| 24 | | 1.33 (3H, t, J = 7.5 Hz), 3.05 (2H, q, J = 7.5 Hz), 6.85-7.25 (4H, m), 7.49 (1H, s), 7.85-8.55 (2H, m), |

TABLE 9-continued
| Ex No. | Str. | ¹H-NMR δ ppm (DMSO-d6) |
|---|---|---|
| 25 | 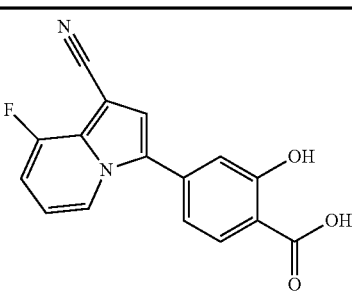 | 6.90-7.05 (1H, m), 7.15-7.35 (3H, m), 7.60 (1H, s), 7.93 (1H, d, J = 8.1 Hz), 8.47 (1H, d, J = 7.0 Hz), |
| 26 | 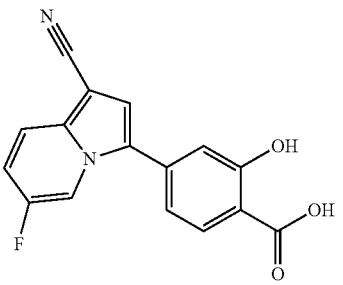 [SMILES: Cc1ccc2c(C#N)cc(-c3ccc(C(=O)O)c(O)c3)n2c1] | 7.20-7.30 (2H, m), 7.35-7.45 (1H, m), 7.60 (1H, s), 7.80-8.00 (2H, m), 8.70-8.80 (1H, m) |
| 27 | 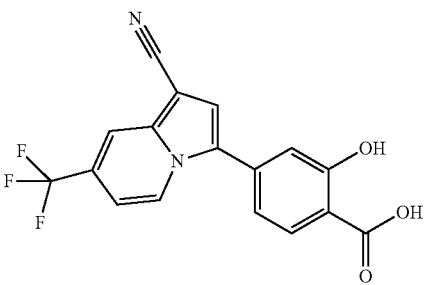 [SMILES: N#Cc1cc(-c2ccc(C(=O)O)c(O)c2)n2ccc(C(F)(F)F)cc12] | 7.00-7.40 (3H, m), 7.74 (1H, s), 7.85-8.85 (3H, m) |
| 28 | 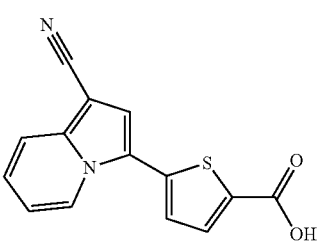 [SMILES: N#Cc1cc(-c2ccc(C(=O)O)s2)n2ccccc12] | 7.00-7.90 (6H, m), 8.60-8.85 (1H, m), 13.38 (1H, brs) |
TABLE 10
| Ex No. | Str. | ¹H-NMR δ ppm (DMSO-d6) |
|---|---|---|
| 29 | 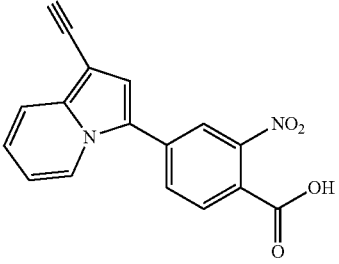 | 6.90-8.30 (7H, m), 8.50-8.80 (1H, m), 14.01 (1H, brs) |

TABLE 10-continued
| Ex No. | Str. | $^1$H-NMR δ ppm (DMSO-d6) |
|---|---|---|
| 30 | 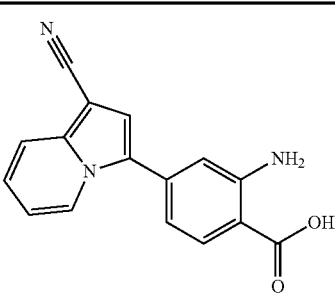 | 6.90-8.00 (7H, m), 8.55-8.75 (1H, m), 12.00 (1H, brs) |
| 31 | 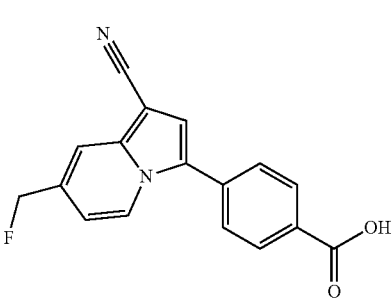 [SMILES: N#Cc1cc(-c2ccc(C(=O)O)cc2)n2ccc(CF)cc12] | 5.55 (2H, d, J = 47.3 Hz), 6.95-7.10 (1H, m), 7.55 (1H, s), 7.65-8.80 (6H, m), 13.1 (1H, brs.) |
| 32 | 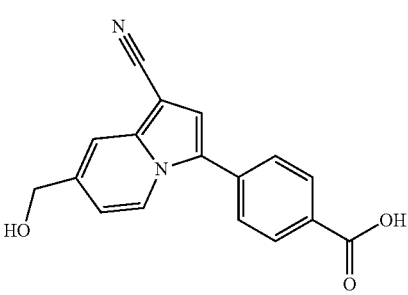 [SMILES: N#Cc1cc(-c2ccc(C(=O)O)cc2)n2ccc(CO)cc12] | 4.56 (2H, s), 5.53 (1H, brs.), 6.85-7.00 (1H, m), 7.48 (1H, s), 7.60-7.70 (1H, m), 7.75-7.85 (2H, m), 8.00-8.15 (2H, m), 8.55-8.65 (1H, m), 13.1 (1H, brs.) |
| 33 | 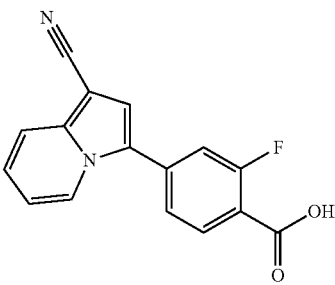 [SMILES: N#Cc1cc(-c2ccc(C(=O)O)c(F)c2)n2ccccc12] | 6.90-7.40 (2H, m), 7.50-8.10 (5H, m), 8.60-8.80 (1H, m), 13.35 (1H, brs) |
| 34 | 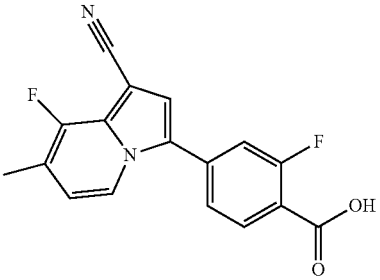 [SMILES: Cc1ccn2c(-c3ccc(C(=O)O)c(F)c3)cc(C#N)c2c1F] | 2.33 (3H, d, J = 1.9 Hz), 6.80-7.05 (1H, m), 7.45-8.60 (5H, m), 13.38 (1H, brs) |

TABLE 10-continued

| Ex No. | Str. | ¹H-NMR δ ppm (DMSO-d6) |
|---|---|---|
| 35 | | 2.40 (3H, s), 2.60 (3H, s), 6.80-6.90 (1H, m), 7.39 (1H, s), 7.50-7.60 (3H, m), 7.96 (1H, d, J = 7.8 Hz), 8.53 (1H, d, J = 7.1 Hz), 12.90 (1H, brs.) |

TABLE 11

| Ex No. | Str. | ¹H-NMR δ ppm (DMSO-d6) |
|---|---|---|
| 36 | | 2.43 (3H, s), 7.51 (1H, s), 7.70-8.15 (5H, m), 8.67 (1H, s), 13.14 (1H, brs) |
| 37 | | 2.42 (3H, s), 6.95 (1H, d, J = 7.3 Hz), 7.54 (1H, s), 7.70-8.15 (4H, m), 8.49 (1H, d, J = 7.3 Hz), 13.18 (1H, brs) |
| 38 | | 2.33 (3H, s), 2.61 (3H, s), 6.70-7.00 (1H, m), 7.43 (1H, s), 7.60-8.60 (5H, m), 13.18 (1H, brs) |
| 39 | | 2.73 (3H, s), 6.90-7.10 (1H, m), 7.53 (1H, s), 7.60-8.50 (5H, m) |

TABLE 11-continued

| Ex No. | Str. | $^1$H-NMR δ ppm (DMSO-d6) |
|---|---|---|
| 40 | (structure: 7,8-difluoro-1-cyano-3-(4-carboxyphenyl)indolizine) | 7.45-7.90 (4H, m), 8.00-8.75 (3H, m), 13.19 (1H, brs) |
| 41 | (structure: 8-methoxy-1-cyano-3-(4-carboxyphenyl)indolizine) | 3.99 (3H, s), 6.60-7.05 (2H, m), 7.41 (1H, s), 7.60-8.30 (5H, m) |
| 42 | (structure: 7-isopropyl-1-cyano-3-(4-carboxyphenyl)indolizine) | 1.26 (6H, d, J = 6.9 Hz), 2.90-3.10 (1H, m), 6.85-7.05 (1H, m), 7.40-7.55 (2H, m), 7.70-8.65 (5H, m), 13.10 (1H, brs) |

TABLE 12

| Ex No. | Str. | $^1$H-NMR δ ppm (DMSO-d6) |
|---|---|---|
| 43 | (structure: 7-tert-butyl-1-cyano-3-(4-carboxyphenyl)indolizine) | 1.34 (9H, s), 7.00-7.55 (3H, m), 7.65-8.65 (5H, m) |
| 44 | (structure: 7-(2-hydroxypropan-2-yl)-1-cyano-3-(4-carboxyphenyl)indolizine) | 1.48 (6H, s), 5.38 (1H, s), 6.90-7.20 (1H, m), 7.47 (1H, s), 7.60-8.65 (6H, m), 13.06 (1H, brs) |

TABLE 12-continued

| Ex No. | Str. | $^1$H-NMR δ ppm (DMSO-d6) |
|---|---|---|
| 45 | | 3.92 (3H, s), 6.60-7.10 (2H, m), 7.35 (1H, s), 7.60-8.20 (4H, m), 8.40-8.60 (1H, m), 13.05 (1H, brs) |
| 46 | | 2.14 (3H, s), 3.95 (3H, s), 6.70 (1H, s), 7.29 (1H, s), 7.65-8.15 (4H, m), 8.40 (1H, s), 13.05 (1H, brs) |
| 47 | | 1.32 (6H, d, J = 6.1 Hz), 4.85-5.05 (1H, m), 7.12 (1H, d, J = 7.8 Hz), 7.45 (1H, s), 7.65-8.15 (4H, m), 8.65 (1H, d), 13.15 (1H, brs) |
| 48 | | 7.20-7.35 (2H, m), 7.78 (1H, s), 7.90-9.05 (3H, m) |
| 49 | | 2.42 (3H, s), 7.10-7.30 (2H, m), 7.52 (1H, s), 7.75-8.00 (2H, m), 8.67 (1H, s) |

TABLE 13
| Ex No. | Str. | ¹H-NMR δ ppm (DMSO-d6) |
|---|---|---|
| 50 | 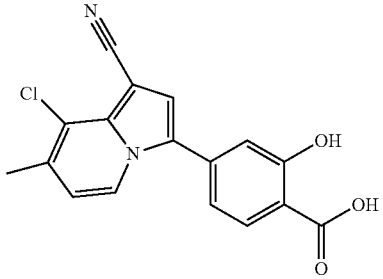 [SMILES: Cc1ccn2c(-c3ccc(C(=O)O)c(O)c3)cc(C#N)c2c1Cl] | 2.42 (3H, s), 6.80-7.25 (3H, m), 7.52 (1H, s), 7.80-8.65 (2H, m) |
| 51 | 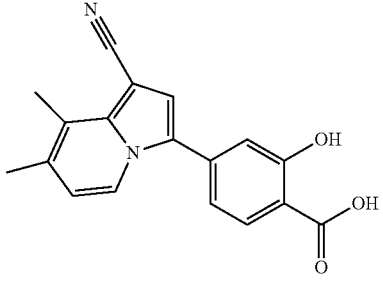 [SMILES: Cc1ccn2c(-c3ccc(C(=O)O)c(O)c3)cc(C#N)c2c1C] | 2.32 (3H, s), 2.60 (3H, s), 6.80-7.25 (3H, m), 7.44 (1H, s), 7.80-8.50 (2H, m) |
| 52 | 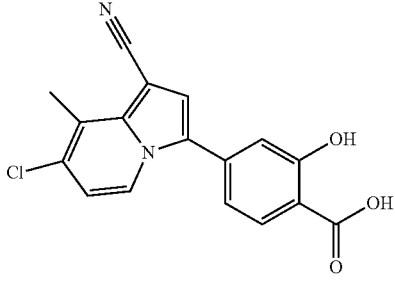 [SMILES: Cc1c(Cl)ccn2c(-c3ccc(C(=O)O)c(O)c3)cc(C#N)c12] | 2.73 (3H, s), 6.90-7.30 (3H, m), 7.54 (1H, s), 7.80-8.60 (2H, m) |
| 53 | 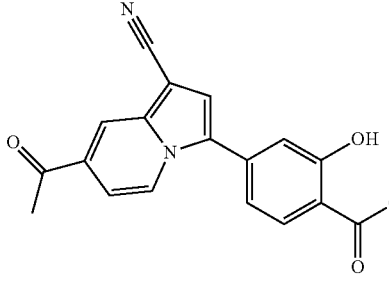 | 2.69 (3H, s), 7.10-7.45 (3H, m), 7.72 (1H, s), 7.85-8.75 (3H, m) |
| 54 | 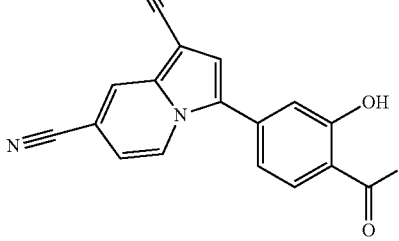 | 7.10-7.45 (3H, m), 7.64 (1H, s), 7.85-8.75 (3H, m) |

TABLE 13-continued
| Ex No. | Str. | ¹H-NMR δ ppm (DMSO-d6) |
|---|---|---|
| 55 | 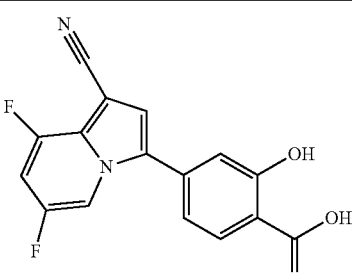 | 7.00-8.10 (5H, m), 8.50-8.75 (1H, m) |
| 56 | 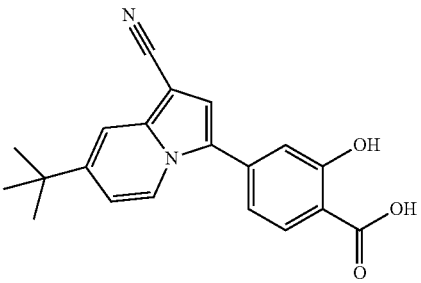 [SMILES: CC(C)(C)c1ccn2c(-c3ccc(C(=O)O)c(O)c3)cc(C#N)c2c1] | 1.34 (9H, s), 7.00-7.55 (3H, m), 7.65-8.65 (4H, m) |
TABLE 14
| Ex No. | Str. | ¹H-NMR δ ppm (DMSO-d6) |
|---|---|---|
| 57 | 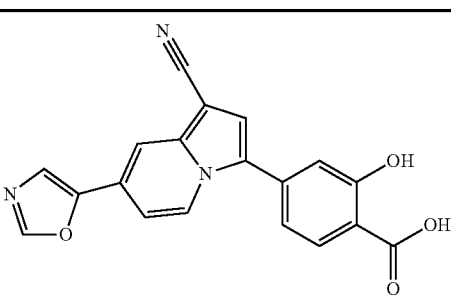 | 7.15-7.40 (3H, m), 7.59 (1H, s), 7.85-8.10 (3H, m), 8.50-8.75 (2H, m) |
| 58 | 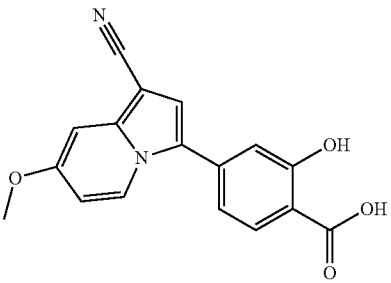 [SMILES: COc1ccn2c(-c3ccc(C(=O)O)c(O)c3)cc(C#N)c2c1] | 3.92 (3H, s), 6.60-8.00 (6H, m), 8.40-8.65 (1H, m) |
| 59 | 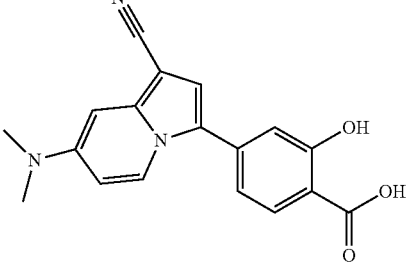 | 3.05 (6H, s), 6.44 (1H, s), 6.70-7.40 (4H, m), 7.70-8.60 (2H, m) |

TABLE 14-continued

| Ex No. | Str. | $^1$H-NMR δ ppm (DMSO-d6) |
|---|---|---|
| 60 | | 2.14 (3H, s), 3.95 (3H, s), 6.95-7.35 (4H, m), 7.80-7.95 (1H, m), 8.35-8.50 (1H, m) |
| 61 | | 7.00-7.50 (2H, m), 7.70-8.20 (5H, m), 8.50-8.65 (1H, m), 13.19 (1H, brs) |
| 62 | | 7.00-7.50 (4H, m), 7.70-8.05 (2H, m), 8.50-8.65 (1H, m) |

TABLE 15

| Ex No. | Str. | $^1$H-NMR δ ppm (DMSO-d6) |
|---|---|---|
| 63 | | 5.54 (2H, d, J = 6.9 Hz), 7.00-7.05 (1H, m), 7.15-7.25 (2H, m), 7.56 (1H, s), 7.80-7.85 (1H, m), 7.90-8.00 (1H, m), 8.67 (1H, d, J = 7.1 Hz) |
| 64 | | 7.05-7.15 (1H, m), 7.55 (1H, s), 7.75-7.85 (2H, m), 8.00-8.15 (3H, m), 8.50-8.60 (1H, m), 12.90-13.40 (1H, m). |

TABLE 15-continued
| Ex No. | Str. | ¹H-NMR δ ppm (DMSO-d6) |
|---|---|---|
| 65 | 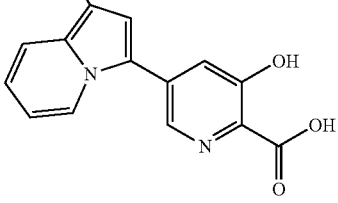 | 6.95-7.40 (2H, m), 7.67 (1H, s), 7.70-7.90 (2H, m), 8.35-8.75 (2H, m) |
| 66 | 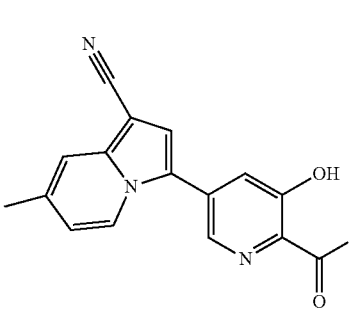 | 2.41 (3H, s), 6.80-7.90 (4H, m), 8.30-8.70 (2H, m) |
| 67 | 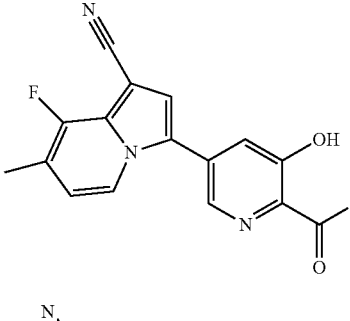 | 2.33 (3H, d, J = 2.1 Hz), 6.85-7.00 (1H, m), 7.66 (1H, s), 7.75-7.85 (1H, m), 8.35-8.55 (2H, m) |
| 68 | 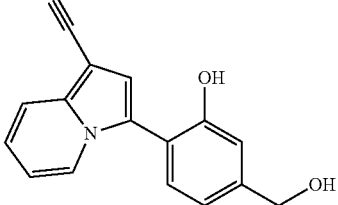 | 6.90-7.00 (1H, m), 7.25-7.30 (1H, m), 7.32 (1H, s), 7.40-7.55 (2H, m), 7.60-7.65 (1H, m), 7.70-7.80 (1H, m), 7.90-8.00 (1H, m), 10.49 (1H, s), 12.85-13.15 (1H, m). |
TABLE 16
| Ex No. | Str. | ¹H-NMR δ ppm (DMSO-d6) |
|---|---|---|
| 69 | | 6.95-7.05 (1H, m), 7.30-7.40 (1H, m), 7.54 (1H, s), 7.75-7.95 (4H, m), 8.20-8.30 (1H, m), 13.48 (1H, brs). |

TABLE 16-continued

| Ex No. | Str. | ¹H-NMR δ ppm (DMSO-d6) |
|---|---|---|
| 70 | 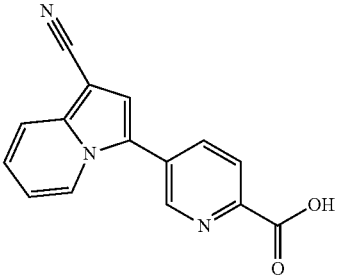 [SMILES: N#Cc1cc(-c2ccc(C(=O)O)nc2)n2ccccc12] | 6.95-7.10 (1H, m), 7.30-7.40 (1H, m), 7.67 (1H, s), 7.80 (1H, d, J = 9.0 Hz), 8.17 (1H, d, J = 8.1 Hz), 8.25-8.35 (1H, m), 8.69 (1H, d, J = 3.0 Hz), 8.95-9.05 (1H, m), 13.3 (1H, brs) |
| 71 | 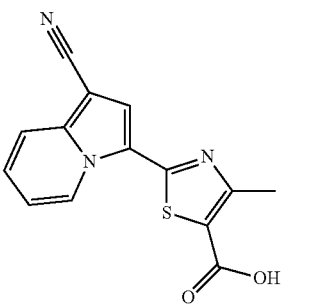 [SMILES: Cc1nc(-c2cc(C#N)c3ccccn23)sc1C(=O)O] | 2.72 (3H, s), 7.25-7.35 (1H, m), 7.45-7.55 (1H, m), 7.80-7.90 (1H, m), 8.17 (1H, s), 9.85-9.90 (1H, m), 13.39 (1H, brs). |
| 72 | 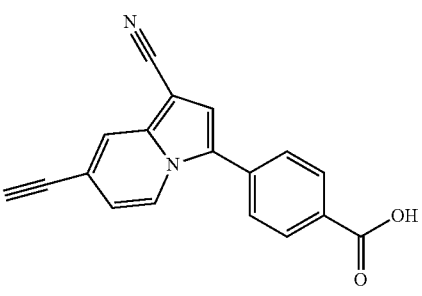 [SMILES: C#Cc1ccn2c(-c3ccc(C(=O)O)cc3)cc(C#N)c2c1] | 4.55 (1H, s), 6.90-7.00 (1H, m), 7.61 (1H, s), 7.75-7.85 (2H, m), 7.85-7.90 (1H, m), 8.05-8.15 (2H, m), 8.55-8.60 (1H, m), 13.11 (1H, brs). |
| 73 | 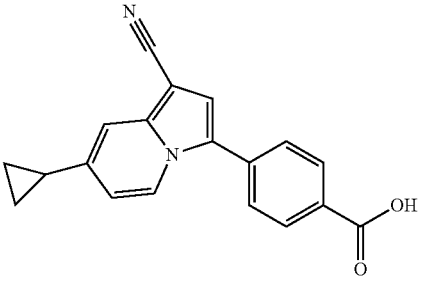 [SMILES: N#Cc1cc(-c2ccc(C(=O)O)cc2)n2ccc(C3CC3)cc12] | 0.80-0.90 (2H, m), 1.00-1.10 (2H, m), 2.05-2.15 (1H, m), 6.65-6.75 (1H, m), 7.43 (1H, s), 7.45-7.50 (1H, m), 7.75 (2H, d, J = 8.5 Hz), 8.06 (2H, d, J = 8.5 Hz), 8.45-8.55 (1H, m) 13.07 (1H, brs). |

TEST EXAMPLE 1

Xanthine Oxidase Inhibitory Activity (1) Preparation of test compounds

Test compounds were dissolved in DMSO (Wako pure chemical) at 40 mM concentration and then diluted to intended concentrations with phosphate-buffered saline (PBS).

(2) Method for measurement

Xanthine oxidase (from bovine milk, Sigma) was prepared with phosphate-buffered saline (PBS) at 0.02 units/mL, and then the solution was added to 96 well plates at 50 μL/well. In addition, test compounds diluted with PBS were added at 50 μL/well. Xanthine (Wako pure chemical) at 200 μM prepared with PBS was added at 100 μL/well, and the mixture was reacted for 10 minutes at room temperature. Absorbance at 290 nm was measured using a microplate reader SpectraMax Plus 384 (Molecular device). The absorbance under a condition without xanthine is 0%, and control without test compounds is 100%. Fifty % inhibitory concentration ($IC_{50}$) of test compounds was calculated (Table 17). Ex. No. in the table indicates Example number.

TABLE 17

| Ex.No. | $IC_{50}$ (nM) |
|---|---|
| 1 | 7 |
| 2 | 4 |
| 3 | 6 |
| 4 | 7 |
| 5 | 10 |

TABLE 17-continued

| EX.No. | IC$_{50}$ (nM) |
| --- | --- |
| 8 | 9 |
| 7 | 5 |
| 8 | 6 |
| 9 | 3 |
| 10 | 8 |
| 11 | 4 |
| 12 | 11 |
| 13 | 9 |
| 14 | 18 |
| 15 | 10 |
| 17 | 4 |
| 18 | 3 |
| 19 | 3 |
| 20 | 5 |
| 21 | 4 |
| 22 | 3 |
| 23 | 3 |
| 24 | 6 |
| 25 | 5 |
| 28 | 3 |
| 27 | 5 |
| 30 | 8 |

| EX.No. | IC$_{50}$ (nM) |
| --- | --- |
| 33 | 30 |
| 34 | 10 |
| 36 | 8 |
| 37 | 4 |
| 38 | 5 |
| 39 | 8 |
| 40 | 14 |
| 41 | 5 |
| 42 | 4 |
| 43 | 2 |
| 44 | 3 |
| 45 | 5 |
| 46 | 8 |
| 47 | 2 |
| 48 | 6 |
| 49 | 2 |
| 50 | 2 |
| 51 | 5 |
| 52 | 2 |
| 53 | 3 |
| 54 | 3 |
| 55 | 6 |
| 56 | 2 |
| 57 | 4 |
| 58 | 2 |
| 59 | 10 |
| 80 | 15 |
| 81 | 68 |
| 62 | 4 |
| 63 | 8 |
| 64 | 8 |
| 65 | 8 |
| 66 | 2 |
| 67 | 2 |
| 70 | 18 |
| 71 | 20 |

TEST EXAMPLE 2

Inhibitory Activity of Uric Acid Transport with Human URAT1 Expressing Cells (1) Preparation of transiently human URAT1 expressing cells Full length human URAT1 cDNA (NCBI Accession No. NM_144585) was subcloned into expression vector, pcDNA3.1 (Invitrogen). Human URAT1 expression vector was transfected into COS7 cells (RIKEN CELL BANK RCB0539) using Lipofectamine 2000 (Invitrogen). COS7 cells were seeded in collagen-coated 24 well plates (Beckton Dickinson) at 3×10$^5$ cells / well and cultured in D-MEM culture medium (Invitrogen) containing 10% fetal bovine serum (Sanko Junyaku) for 2 hours at 37° C. under the condition of 5% CO$_2$. For 1 well, 2 μL of Lipofectamine 2000 was diluted in 50 μL of OPTI-MEM (Invitrogen) and allowed to stand at room temperature for 7 minutes (hereinafter referred to as Lipo2000-OPTI). For 1 well, 0.8 μg of human URAT1 expression vector was diluted in 50 μL of OPTI-MEM (Invitrogen) and combined gently with Lipo2000-OPTI. After standing at room temperature for 25 minutes, the mixture was added to COS7 cells at 100 μL/well. Furthermore, COS7 cells were cultured for 2 days at 37° C. under the condition of 5% CO$_2$ and used for measuring inhibitory activity on the uptake.

(2) Preparation of test compounds

Test compounds were dissolved in DMSO (Wako pure chemical) at 10 mM concentration and then diluted to 2 times higher concentration than intended with pre-treatment buffer (125 mM sodium gluconate, 4.8 mM potassium gluconate, 1.2 mM potassium dihydrogen phosphate, 1.2 mM magnesium sulfate, 1.3 mM calcium gluconate, 5.6 mM glucose, 25 mM Hepes, pH 7.4). Pre-treatment buffer without test compounds was used for control. In addition, an equal volume of pre-treatment buffer containing $^{14}$C-labeled uric acid (American Radiolabeled Chemicals, Inc.) was added to test compounds and control, and finally assay buffer including 20 μM uric acid was prepared.

(3) Method for measurement

All tests were performed on hot-plate at 37° C. Pre-treatment buffer and assay buffer were incubated at 37° C. and then used for assays. Medium was removed from plates, and 700 μL of pre-treatment buffer was added, and the cells were pre-incubated for 10 minutes. After repeating the same step, pre-treatment buffer was removed, and assay buffer was added at 400 μL/well. The uptake reaction was carried out for 5 minutes. After terminating the reaction, assay buffer was rapidly removed, and the cells were washed twice with addition of ice-cold pre-treatment buffer at 1.2 mL/well. Then, the cells were lysed by addition of 0.2 mol/L sodium hydroxide at 300 μL/well. The lysed solutions were transferred into Picoplate (PerkinElmer), and Microscinti 40 (PerkinElmer) was added at 600 μL/well. After mixing, the radioactivity was counted in a liquid scintillation counter (PerkinElmer). The radioactivity in COS7 cells not transfected with URAT1 expression vector was also counted under the same condition as control. As a result, it was shown that compounds of Examples 5, 8, 17, 18, 22, 40 and 55 have inhibitory activity of 50% or higher in a concentration of 10 μM.

TEST EXAMPLE 3

Serum Hypouricemic Effect

Test compounds at 1 mg/kg suspended in 0.5% methylcellulose solution were administered by oral gavage administration to overnight fasted male CD (SD) IGS rats (5-week-old, Charls River Japan). At 2 hours after administration, blood was collected under ether anesthesia from abdominal aorta, and serum was separated according to general method. Serum uric acid values were determined by use of uric acid measurement kit (Uric acid C-Test Wako: Wako pure chemical), and percent decrease in uric acid was calculated according to the formula described below. As a result, it was shown that compounds of Examples 2, 7, 10, 22, 23, 25, 37, 49, 50 and 58 have over 60% percent decrease in uric acid.

Percent decrease in uric acid (%)=(Serum uric acid values in control animals−Serum uric acid values in animals administered test compounds)×100/Serum uric acid values in control animals Industrial Applicability The indolizine derivatives represented by the formula (I) of the present invention or prodrugs thereof, or pharmaceutically acceptable salts thereof exert an excellent xanthine oxidase inhibitory activity, and therefore, can exert an inhibitory activity of uric acid production and lower the serum uric acid level. Therefore, the present invention can provide an agent for the prevention or treatment of hyperuricemia, gouty tophus, gouty arthritis, renal disorder associated with hyperuricemia, urinary calculi or the like.

The invention claimed is:

1. An indolizine derivative represented by the formula (I):

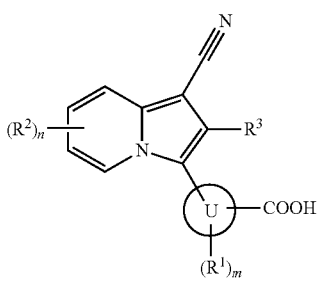

(I)

wherein
ring U represents aryl or heteroaryl;
$R^1$ represents a halogen atom, a hydroxy group, nitro, amino or $C_{1-6}$ alkyl which may be substituted by a fluorine atom;
$R^2$ represents any of the following (1) to (7):
(1) a halogen atom;
(2) a hydroxy group;
(3) amino;
(4) carbamoyl;
(5) cyano;
(6) carboxy;
(7) $C_{1-6}$ alkyl, $C_{2-6}$ alkenyl, $C_{2-6}$ alkynyl, $C_{1-6}$ alkoxy, mono(di) $C_{1-6}$ alkylamino, $C_{2-7}$ acyl, $C_{2-7}$ acylamino, mono(di)$C_{1-6}$ alkylcarbamoyl, $C_{1-6}$ alkylsulfonyl, $C_{1-6}$ alkylsulfonylamino, mono(di)$C_{1-6}$ alkylsulfamoyl, $C_{1-6}$ alkylthio, $C_{2-6}$ alkenyl $C_{1-6}$ alkoxy, $C_{3-8}$ cycloalkyl, 3 to 8-membered heterocycloalkyl, $C_{5-8}$ cycloalkenyl, 5 to 8-membered heterocycloalkenyl, $C_{3-8}$ cycloalkyloxy, $C_{3-8}$ cycloalkylamino, $C_{3-8}$ cycloalkyl $C_{1-6}$ alkyl, $C_{3-8}$ cycloalkyl $C_{1-6}$ alkoxy, $C_{3-8}$ cycloalkyl $C_{1-6}$ alkylamino, aryl, heteroaryl, aryloxy, arylamino, arylcarbonyl, arylcarbonylamino, aryl$C_{1-6}$ alkoxy, heteroaryloxy, heteroarylamino, heteroarylcarbonyl or heteroarylcarbonylamino each of which may have any group selected from substituent group α;
m represents an integral number from 0 to 2, and when m is 2, these $R^1$ are optionally different from each other;
n represents an integral number from 0 to 3, and when n is 2 or 3, these $R^2$ are optionally different from each other; and when two $R^2$ bound to the neighboring atoms in the indolizine ring exist and independently represent a group selected from the group consisting of $C_{1-6}$ alkyl which may be substituted by a fluorine atom and $C_{1-6}$ alkoxy which may be substituted by a fluorine atom, these two $R^2$ optionally form a 5 to 8-membered ring together with the binding atoms in the indolizine ring;
$R^3$ represents a hydrogen atom, a chlorine atom or a fluorine atom; and substituent group α consists of a fluorine atom, a chlorine atom, a hydroxy group, amino, carboxy, carbamoyl, cyano, $C_{1-6}$ alkyl, $C_{1-6}$ alkoxy and mono(di)$C_{1-6}$ alkylamino, or a pharmaceutically acceptable salt thereof.

2. An indolizine derivative as claimed in claim 1, represented by the formula (Ia):

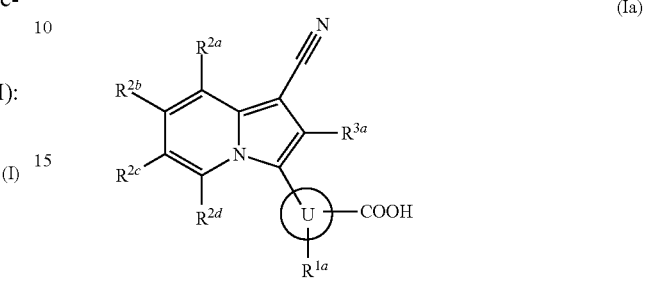

(Ia)

wherein
ring U represents aryl or heteroaryl;
$R^{1a}$ represents a hydrogen atom, a fluorine atom, a hydroxy group, amino, methyl or trifluoromethyl;
$R^{2a}$ and $R^{2b}$ independently represent any of the following (a1) to (a4):
(a1) a hydrogen atom;
(a2) a halogen atom;
(a3) a hydroxy group;
(a4) $C_{1-6}$ alkyl, $C_{1-6}$ alkoxy, mono(di)$C_{1-6}$ alkylamino, $C_{2-7}$ acyl, $C_{1-6}$ alkylthio, $C_{3-8}$ cycloalkyl, 3 to 8-membered heterocycloalkyl, aryl or heteroaryl each of which may have any group selected from substituent group α;
$R^{2c}$ represents a hydrogen atom, a halogen atom, a hydroxy group, $C_{1-6}$ alkyl which may have any group selected from substituent group α or $C_{1-6}$ alkoxy which may have any group selected from substituent group α, or
when $R^{2a}$ and $R^{2b}$, or $R^{2b}$ and $R^{2c}$ independently represent a group selected from the group consisting of $C_{1-6}$ alkyl which may be substituted by a fluorine atom and $C_{1-6}$ alkoxy which may be substituted by a fluorine atom, they optionally form a 5 to 8-membered ring together with the binding atoms in the indolizine ring;
$R^{2d}$ represents a hydrogen atom or a fluorine atom;
$R^{3a}$ represents a hydrogen atom or a fluorine atom; and
substituent group α has the same meaning as described in claim 1, or a pharmaceutically acceptable salt thereof.

3. An indolizine derivative as claimed in claim 2, wherein ring U represents a benzene ring, a pyridine ring, a thiophene ring or a thiazole ring, or a pharmaceutically acceptable salt thereof.

4. An indolizine derivative as claimed in claim 2, wherein the group represented by the formula:

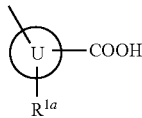

is a group represented by the formula:
and $R^{1a}$ represents a hydrogen atom or a hydroxy group, or a pharmaceutically acceptable salt thereof.

5. An indolizine derivative as claimed in claim 3, wherein $R^{2a}$ and $R^{2b}$ independently represent any of the following (b1) to (b4):
- (b1) a hydrogen atom;
- (b2) a halogen atom;
- (b3) a hydroxy group;
- (b4) $C_{1-6}$ alkyl, $C_{1-6}$ alkoxy, mono(di)$C_{1-6}$ alkylamino or hydroxy $C_{1-6}$ alkyl each of which may be substituted by a fluorine atom; and $R^{2c}$ represents a hydrogen atom, a halogen atom, a hydroxy group, $C_{1-6}$ alkyl which may be substituted by a fluorine atom or $C_{1-6}$ alkoxy which may be substituted by a fluorine atom, or a pharmaceutically acceptable salt thereof.

6. An indolizine derivative as claimed in claim 2, wherein $R^{2d}$ represents a hydrogen atom, or a pharmaceutically acceptable salt thereof.

7. An indolizine derivative as claimed in claim 1, wherein $R^3$ or $R^{3a}$ represents a hydrogen atom, or a pharmaceutically acceptable salt thereof.

8. An indolizine derivative as claimed in claim 6, wherein $R^{1a}$ represents a hydrogen atom or a hydroxy group;

$R^{2a}$ represents a hydrogen atom, a fluorine atom, a chlorine atom, methyl, ethyl, methoxy, monofluoromethyl, difluoromethyl, trifluoromethyl, difluoromethoxy or trifluoromethoxy;

$R^{2b}$ represents a hydrogen atom, a fluorine atom, a chlorine atom, methyl, ethyl, methoxy, monofluoromethyl, difluoromethyl, trifluoromethyl, difluoromethoxy or trifluoromethoxy; and $R^{2c}$ represents a hydrogen atom, a fluorine atom, a chlorine atom, methyl, monofluoromethyl, difluoromethyl or trifluoromethyl, or a pharmaceutically acceptable salt thereof.

9. An indolizine derivative as claimed in claim 8, wherein $R^{2b}$ represents a hydrogen atom, methyl, ethyl, methoxy, monofluoromethyl, difluoromethyl, trifluoromethyl, difluoromethoxy or trifluoromethoxy, or a pharmaceutically acceptable salt thereof.

10. An indolizine derivative as claimed in claim 8, wherein $R^{1a}$ represents a hydrogen atom, or a pharmaceutically acceptable salt thereof.

11. An indolizine derivative as claimed in claim 9, wherein $R^{1a}$ represents a hydroxy group, or a pharmaceutically acceptable salt thereof.

12. An indolizine derivative as claimed in claim 1, which is a xanthine oxidase inhibitor, or a pharmaceutically acceptable salt thereof.

13. A pharmaceutical composition comprising as an active ingredient an indolizine derivative as claimed in claim 1, or a pharmaceutically acceptable salt thereof and a pharmaceutical additive.

14. A pharmaceutical composition as claimed in claim 13, which is an agent for lowering serum uric acid level.

15. A pharmaceutical composition as claimed in claim 13, which is a uric acid production inhibitor.

16. An indolizine derivative as claimed in claim 1, which is selected from the group consisting of
- 4-(1-cyanoindolizine-3-yl) benzoic acid,
- 4-(1-cyano-7-methylindolizine-3-yl) benzoic acid,
- 4-(8-chloro-1- cyanoindolizine-3-yl) benzoic acid,
- 4-(1-cyano-8-methylindolizine-3-yl) benzoic acid,
- 4-(1-cyano-6-methylindolizine-3-yl) benzoic acid,
- 4-(1-cyano-6, 8-dimethylindolizine-3-yl) benzoic acid,
- 4-(1-cyano-8-fluoro-7-methylindolizine-3-yl) benzoic acid,
- 4-(1-cyano-6-fluoro-7-methylindolizine-3-yl) benzoic acid,
- 4-(1-cyano-7-ethylindolizine-3-yl) benzoic acid,
- 4-(1-cyano-8-ethylindolizine-3-yl) benzoic acid,
- 4-(1-cyano-8-fluoroindolizine-3-yl) benzoic acid,
- 4-(1-cyano-6-fluoroindolizine-3-yl) benzoic acid,
- 4-(1-cyano-7-trifluoromethylindolizine-3-yl) benzoic acid,
- 4-(1-cyanoindolizine-3-yl)-2-hydroxybenzoic acid,
- 4-(1-cyano-7-methylindolizine-3-yl)-2-hydroxybenzoic acid,
- 4-(1-cyano-8-methylindolizine-3-yl)-2-hydroxybenzoic acid,
- 4-(1-cyano-6-methylindolizine-3-yl)-2-hydroxybenzoic acid,
- 4-(1-cyano-6, 8-dimethylindolizine-3-yl)-2-hydroxybenzoic acid,
- 4-(1-cyano-6-fluoro-7-methylindolizine-3-yl)-2-hydroxybenzoic acid,
- 4-(1-cyano-8-fluoro-7-methylindolizine-3-yl)-2-hydroxybenzoic acid,
- 4-(1-cyano-8-ethylindolizine-3-yl)-2-hydroxybenzoic acid,
- 4-(1-cyano-8-fluoroindolizine-3-yl)-2-hydroxybenzoic acid,
- 4-(1-cyano-6-fluoroindolizine-3-yl)-2-hydroxybenzoic acid,
- 4-(1-cyano-7-trifluoromethylindolizine-3-yl)-2-hydroxybenzoic acid,
- 4-(1-cyano-7-fluoromethylindolizine-3-yl) benzoic acid,
- 4-(6-chloro-1-cyano-7-methylindolizine-3-yl) benzoic acid,
- 4-(8-chloro-1-cyano-7-methylindolizine-3-yl) benzoic acid,
- 4-(1-cyano-7, 8-dimethylindolizine-3-yl) benzoic acid,
- 4-(7-chloro-1-cyano-8-methylindolizine-3-yl) benzoic acid,
- 4-(1-cyano-6, 8-difluoroindolizine-3-yl) benzoic acid,
- 4-(1-cyano-8-methoxyindolizine-3-yl) benzoic acid,
- 4-(1-cyano-7-methoxyindolizine-3-yl) benzoic acid,
- 4-(1-cyano-7-methoxy-6-methylindolizine-3-yl) benzoic acid,
- 4-(1-cyano-6-fluoro-7-trifluoromethylindolizine-3-yl)-2-hydroxybenzoic acid,
- 4-(6-chloro-1-cyano-7-methylindolizine-3-yl)-2-hydroxybenzoic acid,
- 4-(8-chloro-1-cyano-7-methylindolizine-3-yl)-2-hydroxybenzoic acid,
- 4-(1-cyano-7, 8-dimethylindolizine-3-yl)-2-hydroxybenzoic acid,
- 4-(7-chloro-1-cyano-8-methylindolizine-3-yl)-2-hydroxybenzoic acid,
- 4-(1-cyano-6, 8-difluoroindolizine-3-yl)-2-hydroxybenzoic acid,
- 4-(1-cyano-7-methoxyindolizine-3-yl)-2-hydroxybenzoic acid,
- 4-(1-cyano-7-methoxy-6-methylindolizine-3-yl)-2-hydroxybenzoic acid, and
- 4-(1-cyano-7-fluoromethylindolizine-3-yl)-2-hydroxybenzoic acid, or a pharmaceutically acceptable salt thereof 17. An indolizine derivative as claimed in claim 16, which is selected from the group consisting of
- 4-(1-cyano-6-methylindolizine-3-yl) benzoic acid,
- 4-(1-cyano-6-fluoro-7-methylindolizine-3-yl) benzoic acid,
- 4-(1-cyanoindolizine-3-yl)-2-hydroxybenzoic acid, 4-(1-cyano-7-methylindolizine-3-yl)-2-hydroxybenzoic acid,
4-(1-cyano-6-fluoro-7-methylindolizine-3-yl)-2-hydroxybenzoic acid,
4-(1-cyano-6,8-difluoroindolizine-3-yl) benzoic acid, and
4-(1-cyano-6,8-difluoroindolizine-3-yl)-2-hydroxybenzoic acid, or a pharmaceutically acceptable salt thereof

18. An indolizine derivative as claimed in claim 16, which is selected from the group consisting of
4-(1-cyano-7-methylindolizine-3-yl) benzoic acid,
4-(1-cyano-8-fluoro-7-methylindolizine-3-yl) benzoic acid,
4-(1-cyano-7-ethylindolizine-3-yl) benzoic acid,
4-(1-cyano-6-fluoro-7-methylindolizine-3-yl)-2-hydroxybenzoic acid,
4-(1-cyano-8-fluoro-7-methylindolizine-3-yl)-2-hydroxybenzoic acid,
4-(1-cyano-8-fluoroindolizine-3-yl)-2-hydroxybenzoic acid,
4-(8-chloro-1-cyano-7-methylindolizine-3-yl) benzoic acid,
4-(6-chloro-1cyano-7-methylindolizine-3-yl)-2-hydroxybenzoic acid,
4-(8-chloro-1-cyano-7-methylindolizine-3-yl)-2-hydroxybenzoic acid, and
4-(1-cyano-7-methoxyindolizine-3-yl)-2-hydroxybenzoic acid, or a pharmaceutically acceptable salt thereof.

19. A method of lowering serum uric acid level comprising administering the pharmaceutical composition of claim 13 to a patient in need thereof.

20. A method of the inhibiting uric acid production comprising administering the pharmaceutical composition of claim 13 to a patient in need thereof.

21. An indolizine derivative represented by the formula (I):

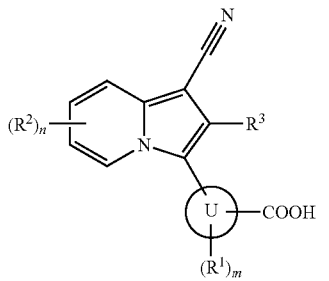

(I)

wherein
ring U represents aryl or heteroaryl;
$R^1$ represents a halogen atom, a hydroxy group, nitro, amino or $C_{1-6}$ alkyl which may be substituted by a fluorine atom;
$R^2$ represents any of the following (1) to (7):
(1) a halogen atom;
(2) a hydroxy group;
(3) amino;
(4) carbamoyl;
(5) cyano;
(6) carboxy;
(7) $C_{1-6}$ alkyl, $C_{2-6}$ alkenyl, $C_{2-6}$ alkynyl, $C_{1-6}$ alkoxy, mono(di) $C_{1-6}$ alkylamino, $C_{2-7}$ acyl, $C_{2-7}$ acylamino, mono(di)$C_{1-6}$alkylcarbamoyl, $C_{1-6}$ alkylsulfonyl, $C_{1-6}$ alkylsulfonylamino, mono(di)$C_{1-6}$ alkylsulfamoyl, $C_{1-6}$ alkylthio, $C_{2-6}$ alkenyl $C_{1-6}$ alkoxy, $C_{3-8}$ cycloalkyl, 3 to 8-membered heterocycloalkyl, $C_{5-8}$ cycloalkenyl, 5 to 8-membered heterocycloalkenyl, $C_{3-8}$ cycloalkyloxy, $C_{3-8}$ cycloalkylamino, $C_{3-8}$ cycloalkyl $C_{1-6}$ alkyl, $C_{3-8}$ cycloalkyl $C_{1-6}$ alkoxy, $C_{3-8}$ cycloalkyl $C_{1-6}$ alkylamino, aryl, heteroaryl, aryloxy, arylamino, arylcarbonyl, arylcarbonylamino, aryl $C_{1-6}$ alkoxy, heteroaryloxy, heteroarylamino, heteroarylcarbonyl or heteroarylcarbonylamino each of which may have any group selected from substituent group α;

m represents an integral number from 0 to 2, and when m is 2, these $R^1$ are optionally different from each other;
n represents an integral number from 0 to 3, and when n is 2 or 3, these $R^2$ are optionally different from each other; and when two $R^2$ bound to the neighboring atoms in the indolizine ring exist and independently represent a group selected from the group consisting of $C_{1-6}$ alkyl which may be substituted by a fluorine atom and $C_{1-6}$ alkoxy which may be substituted by a fluorine atom, these two $R^2$ optionally form a 5 to 8-membered ring together with the binding atoms in the indolizine ring;
$R^3$ represents a hydrogen atom, a chlorine atom or a fluorine atom;
substituent group a consists of a fluorine atom, a chlorine atom, a hydroxy group, amino, carboxy, carbamoyl, cyano, $C_{1-6}$ alkyl, $C_{1-6}$ alkoxy and mono(di)$C_{1-6}$ alkylamino, and wherein the formula contains one or more groups selected from the group consisting of a hydroxy group and an amino group substituted by:
$C_{1-6}$ alkyl-CO—;
aryl-CO—;
$C_{1-6}$ alkyl-O—$C_{1-6}$ alkylene-CO—;
$C_{1-6}$ alkyl-OCO—$C_{1-6}$ alkylene-CO—;
$C_{1-6}$ alkyl-OCO—;
$C_{1-6}$ alkyl-O—$C_{1-6}$ alkylene-OCO—;
$C_{1-6}$ alkyl-COO—$C_{1-6}$ alkylene;
$C_{1-6}$ alkyl-OCOO—$C_{1-6}$ alkylene; or
$C_{3-8}$ cycloalkyl-OCOO—$C_{1-6}$ alkylene;
and a carboxy groups substituted by:
$C_{1-6}$ alkyl;
$C_{1-6}$ alkyl-COO—$C_{1-6}$ alkylene;
$C_{1-6}$ alkyl-OCOO—$C_{1-6}$ alkylene;
$C_{3-8}$ cycloalkyl-OCOO—$C_{1-6}$ alkylene;
mono(di)hydroxy $C_{1-6}$ alkyl;
mono(di)hydroxy $C_{1-6}$ alkyl-OCOO—$C_{1-6}$ alkylene;
$C_{1-6}$ alkoxy $C_{1-6}$ alkoxy $C_{1-6}$ alkyl;
mono(di)$C_{1-6}$ alkylamino $C_{1-6}$ alkyl;
3 to 8-membered heterocycloalkyl $C_{1-6}$ alkyl; or
$C_{1-6}$ alkyl-OCO-amino$C_{1-6}$ alkylene;
or a pharmaceutically acceptable salt thereof.

22. 4-(1-Cyano-7-methylindolizine-3-yl) benzoic acid, or a pharmaceutically acceptable salt thereof.

23. 4-(1-Cyano-8-fluoro-7-methylindolizin-3-yl)-benzoic acid, or a pharmaceutically acceptable salt thereof.

24. 4-(1-Cyanoindolizine-3-yl)-2-hydroxybenzoic acid, or a pharmaceutically acceptable salt thereof.

25. 4-(1-Cyano-7-methylindolizine-3-yl)-2-hydroxybenzoic acid, or a pharmaceutically acceptable salt thereof.

26. 4-(1-Cyano-8-fluoro-7-methylindolizine-3-yl)-2-hydroxybenzoic acid, or a pharmaceutically acceptable salt thereof.

* * * * *